(12) United States Patent
Pathak et al.

(10) Patent No.: US 11,373,102 B2
(45) Date of Patent: Jun. 28, 2022

(54) SENSING AND ACTIVITY CLASSIFICATION FOR INFANTS

(71) Applicants: Verily Life Sciences LLC, South San Francisco, CA (US); The Procter & Gamble Company, Cincinnati, OH (US)

(72) Inventors: Anupam Pathak, Los Altos Hills, CA (US); David He, Foster City, CA (US); Marty Gardner, Melrose, MA (US); Blanca Arizti, Schmitten (DE)

(73) Assignees: THE PROCTER & GAMBLE COMPANY, Cincinnati, OH (US); VERILY LIFE SCIENCES LLC, South San Francisco, CA (US)

( * ) Notice: Subject to any disclaimer, the term of this patent is extended or adjusted under 35 U.S.C. 154(b) by 536 days.

(21) Appl. No.: 16/383,136

(22) Filed: Apr. 12, 2019

(65) Prior Publication Data

US 2019/0340515 A1    Nov. 7, 2019

Related U.S. Application Data

(60) Provisional application No. 62/666,987, filed on May 4, 2018.

(51) Int. Cl.
*G06N 5/02* (2006.01)
*G06N 20/00* (2019.01)

(52) U.S. Cl.
CPC .............. *G06N 5/02* (2013.01); *G06N 20/00* (2019.01)

(58) Field of Classification Search
None
See application file for complete search history.

(56) References Cited

U.S. PATENT DOCUMENTS

| | | | |
|---|---|---|---|
| 3,013,257 | A | 12/1961 | Carmelo |
| 3,261,987 | A | 7/1966 | Chapin |

(Continued)

FOREIGN PATENT DOCUMENTS

| | | |
|---|---|---|
| CN | 205246547 | 5/2016 |
| CN | 106198538 | 12/2016 |

(Continued)

OTHER PUBLICATIONS

Lara, Oscar D., and Miguel A. Labrador. "A survey on human activity recognition using wearable sensors." IEEE communications surveys & tutorials 15.3 (2012): 1192-1209. (Year: 2012).*

(Continued)

*Primary Examiner* — Vincent Gonzales
(74) *Attorney, Agent, or Firm* — Kilpatrick Townsend & Stockton LLP

(57) ABSTRACT

Various examples are described for using a movement sensor to detecting an activity of an infant. In an example, an activity classification system includes a sensor configured to measure the activity of an infant and an external monitor. The monitor receives, from a sensor, a time series of data comprising an inertial measurement for each a time period. The monitor determines, from the time series and by using a predictive model, an activity from a list of identified activities. Examples of identified activities are deep sleep, light sleep, sitting, awake, nursing, or bottle feeding.

25 Claims, 21 Drawing Sheets
(11 of 21 Drawing Sheet(s) Filed in Color)

(56) References Cited

U.S. PATENT DOCUMENTS

| | | | |
|---|---|---|---|
| 4,315,159 A | 2/1982 | Niwa et al. | |
| 5,069,214 A | 12/1991 | Samaras et al. | |
| 5,079,541 A | 1/1992 | Moody | |
| 5,616,140 A | 4/1997 | Prescott et al. | |
| 5,654,803 A | 8/1997 | Howard, III et al. | |
| 6,147,592 A | 11/2000 | Ulrich et al. | |
| 6,287,253 B1 | 9/2001 | Ortega et al. | |
| 8,111,165 B2 | 2/2012 | Ortega et al. | |
| 8,416,088 B2 | 4/2013 | Ortega et al. | |
| 8,628,506 B2 | 1/2014 | Ales, III et al. | |
| 8,920,332 B2 | 12/2014 | Hong et al. | |
| 8,935,006 B2 * | 1/2015 | Vu | B25J 11/008 700/264 |
| 10,117,598 B1 | 11/2018 | Mouradian | |
| 2002/0124295 A1 | 9/2002 | Fenwick et al. | |
| 2004/0022053 A1 | 2/2004 | Sharon et al. | |
| 2005/0019508 A1 | 1/2005 | Engel et al. | |
| 2008/0021429 A1 | 1/2008 | Klofta et al. | |
| 2008/0262381 A1 * | 10/2008 | Kolen | A61B 5/4818 600/595 |
| 2009/0157025 A1 | 6/2009 | Song et al. | |
| 2009/0275908 A1 | 11/2009 | Song | |
| 2010/0164733 A1 | 7/2010 | Ales et al. | |
| 2010/0241094 A1 * | 9/2010 | Sherron | A61F 13/42 604/361 |
| 2010/0290948 A1 | 11/2010 | Song | |
| 2012/0116337 A1 * | 5/2012 | Ales | A61F 13/49009 604/361 |
| 2012/0310192 A1 | 12/2012 | Suzuki et al. | |
| 2013/0001422 A1 | 1/2013 | Lavon et al. | |
| 2013/0066289 A1 | 3/2013 | Song et al. | |
| 2014/0143183 A1 | 5/2014 | Sigal et al. | |
| 2014/0200538 A1 | 7/2014 | Euliano et al. | |
| 2015/0061863 A1 * | 3/2015 | Barfield, Jr. | G08B 21/043 340/539.12 |
| 2015/0150732 A1 | 6/2015 | Abir | |
| 2015/0164377 A1 * | 6/2015 | Nathan | A61B 5/6802 600/595 |
| 2015/0272482 A1 | 10/2015 | Houmanfar et al. | |
| 2015/0288877 A1 * | 10/2015 | Glazer | A61B 5/1114 348/77 |
| 2016/0120455 A1 | 5/2016 | Pop et al. | |
| 2016/0256086 A1 | 9/2016 | Byrd et al. | |
| 2016/0287074 A1 * | 10/2016 | Pradeep | G09B 19/025 |
| 2016/0287076 A1 | 10/2016 | Pradeep et al. | |
| 2016/0292576 A1 | 10/2016 | Pradeep et al. | |
| 2016/0292584 A1 | 10/2016 | Weinberg et al. | |
| 2016/0296144 A1 | 10/2016 | Gaddam et al. | |
| 2017/0049336 A1 | 2/2017 | Hatch | |
| 2017/0128274 A1 | 5/2017 | Varga et al. | |
| 2017/0215808 A1 | 8/2017 | Shimol et al. | |
| 2017/0252225 A1 | 9/2017 | Arizti et al. | |
| 2017/0348162 A1 | 12/2017 | Arizti et al. | |
| 2017/0354547 A1 | 12/2017 | Abir | |
| 2018/0008478 A1 | 1/2018 | Xu | |
| 2018/0056128 A1 | 3/2018 | Narasimha Rao et al. | |
| 2018/0253957 A1 | 9/2018 | Jhangiani et al. | |
| 2019/0342973 A1 | 11/2019 | Schiffer et al. | |
| 2020/0129380 A1 * | 4/2020 | Sazonov | A61J 9/001 |
| 2020/0163602 A1 | 5/2020 | Pareddy et al. | |
| 2020/0323450 A1 | 10/2020 | He | |
| 2020/0323700 A1 | 10/2020 | Schiffer et al. | |
| 2021/0068235 A1 | 3/2021 | Schiffer et al. | |

FOREIGN PATENT DOCUMENTS

| | | |
|---|---|---|
| EP | 2425771 | 3/2012 |
| EP | 2832323 | 2/2015 |
| JP | S61296239 | 12/1986 |
| WO | 0100117 | 1/2001 |
| WO | 02063260 | 8/2002 |
| WO | 2007128038 | 11/2007 |

OTHER PUBLICATIONS

S. Russell and P. Norvig, Artificial Intelligence: A Modern Approach, 2nd Ed., 2003, pp. 649-789. (Year: 2003).*

U.S. Appl. No. 15/971,306 , "Notice of Allowance", dated Oct. 22, 2019, 9 pages.

Chinese Application No. 201920639694.1 , "Office Action", dated Mar. 27, 2020, 3 pages.

International Application No. PCT/US2019/030691 , "International Search Report and Written Opinion", dated Dec. 5, 2019, 18 pages.

U.S. Appl. No. 15/971,306 , "Final Office Action", dated Aug. 8, 2019, 8 pages.

Kastle et al., "A New Family of Sensors for Pulse Oximetry", Hewlett Packard Journal, vol. 48, Article 7, Feb. 1997, pp. 1-17.

Kim et al., "Miniaturized Battery-Free Wireless Systems for Wearable Pulse Oximetryy", Advanced Functional Materials, vol. 27 No. 1, 1604373., Jan. 5, 2017, pp. 1-18.

Leonard et al., "Standard Pulse Oximeters Can be Used to Monitor Respiratory Rate", Emergency Medicine Journal, vol. 20, No. 6, Nov. 2003, pp. 524-525.

International Application No. PCT/US2019/030684 , "International Search Report and Written Opinion", dated Jun. 25, 2019, 11 pages.

International Application No. PCT/US2019/030691, "Invitation to Pay and Partial International Search Report" dated Jul. 30, 2019, 13 pages.

U.S. Appl. No. 15/971,306 , "Non-Final Office Action", dated Jan. 28, 2019, 12 pages.

International Application No. PCT/US2019/030691 , "International Search Report and Written Opinion", dated Sep. 23, 2019, 15 pages.

U.S. Appl. No. 16/745,771, "Ex Parte Quayle Action", dated Jun. 29, 2020, 6 pages.

U.S. Appl. No. 16/745,771, "Notice of Allowance", dated Aug. 24, 2020, 6 pages.

International Application No. PCT/US2020/027920, International Search Report and Written Opinion, dated Jul. 24, 2020, 10 pages.

U.S. Appl. No. 16/949,759, Notice of Allowance, dated Nov. 24, 2021, 11 pages.

U.S. Appl. No. 16/841,129, Non-Final Office Action, dated Feb. 17, 2022, 17 pages.

* cited by examiner

SENSING AND ACTIVITY CLASSIFICATION FOR INFANTS

CROSS-REFERENCES TO RELATED APPLICATIONS

This patent application claims priority to U.S. Provisional Application No. 62/666,987, filed May 4, 2018, which is incorporated herein by reference in its entirety for all purposes.

FIELD

The present application generally relates to electronically detecting activity, but more specifically relates to sensing and activity classification for infants. In a particular example, an activity classification system senses that an infant wearing a sensor is performing a specific activity such as sitting up or sleeping.

BACKGROUND

The overall health and well-being of infants is of paramount concern to parents and other caregivers. Moreover, for new parents, adapting a newborn to sleeping and feeding cycles can be difficult, often causing stress. Hence, determining and recording the activity of infants such as whether the infant is sleeping, sitting up, or feeding, can be useful.

Solutions exist for tracking the activity of adults. For example, fitness and sleep trackers can track exercise such as steps taken, sleep cycles, and more. But these solutions are not adapted to the unique requirements of infants. For example, adult fitness trackers are unfit to be worn by infants.

Existing infant monitoring solutions also suffer from deficiencies. For example, solutions that simply transmit audio from an infant's room to the parents cannot measure activity or sleep. Some products measure an infant's blood oxygenation, alerting the parents if the infant's blood oxygen level drops below a certain threshold. But these solutions require cumbersome sensors to be attached to the infant, which requires skin contact, and can be kicked off. Camera-based infant monitoring solutions exist also, but such camera-based systems simply indicate the presence of the infant. Some camera-based solutions use artificial intelligence but still cannot discern small movements from large movements. As such, these solutions lack the precision to determine the activity of the infant, such as whether the infant is in a light sleep or deep sleep.

SUMMARY

Various examples are described for using a movement sensor to detecting an activity of an infant. In an example, an activity classification system includes a sensor configured to measure the activity of an infant and a monitor. An accelerometer or a gyroscope detects a set of inertial measurements in three dimensions for a time period. A monitor receives the set of inertial measurements. The monitor calculates a variance of the inertial measurement measurements or a root-mean-square of the inertial measurements. The monitor provides the inertial measurements and either the variance or the root-mean-square of the inertial measurements to a predictive model. The monitor receives from the predictive model, a determined activity from a set of predefined activities based on the measurements. The monitor provides the determined activity to an output device.

In an aspect, the statistical data includes (i) a variance of the inertial measurements, or (ii) a root-mean-square of the inertial measurements.

In an aspect, the predefined activities includes one or more of (i) asleep, (ii) awake, (iii) lying on abdomen, (iv) lying on back, (v) settled, or (vi) stirring. In an aspect, the predefined activities includes (i) awake, (ii) asleep, (iii) stirring, or (iv) settled.

In an aspect, the monitor further adjusts the determined activity. For example, when the determined activity is settled, the monitor changes the determined activity to a different state. When the determined activity is stirring, the monitor changes the determined activity to asleep. When the determined activity is (i) asleep, is (ii) below a time threshold, and (iii) occurred during daytime, the monitor changes the determined activity to awake. When the determined activity is (i) awake, is (ii) below a threshold in time, and (iii) occurred during nighttime, the monitor changes the determined activity to asleep.

In an aspect, the predefined activities comprise (i) whether an infant is nursing, (ii) whether the infant was bottle feeding, or (iii) an orientation of the infant during feeding. The monitor further receives, from a gyroscope, a orientation or angular velocity measurements. The monitor provides the orientation or angular velocity measurements to the predictive model. The determined activity is based at least in part on the angular velocity measurements.

In an aspect, the monitor receives training data including time series data indicating inertial measurements measured over a time periods. The training data annotated with a training labels indicating, for each time period, a corresponding activity of a activities. The monitor further iteratively adjusts the predictive model based on a loss function that is based on a comparison of a prediction to a respective training label. Iteratively adjusting the predictive model includes determining, by the predictive model, a prediction of whether data corresponding to a time period corresponds to one of the activities, and modifying the predictive model such that a subsequent value of the loss function is decreased in a subsequent iteration.

In an aspect, the monitor further receives, from a monitor device, additional training data including time series data that indicates inertial measurements measured over an additional time period. The additional training data can be annotated with a training label indicating a corresponding activity of a activities. The monitor further updates the predictive model based on the additional training data and a loss function. The updating includes determining, by the predictive model, a prediction of whether data corresponding to a time period corresponds to one of the activities. The updating further includes reducing a value of the loss function based on a comparison of the prediction to the training label.

In an aspect, the monitor further receives training data including time series data indicating inertial measurements measured over time periods. The training data is annotated with a training labels indicating, for each time period, whether an infant was awake or asleep. The monitor further trains the predictive model based on the training data and a loss function. The training can include: determining, by the predictive model, a prediction of (i) awake, (ii) asleep, (iii) stirring, or (iv) settled, and minimizing the loss function based of a comparison of the prediction to the training label.

In an aspect, the monitor further stores in a memory, time series data for a set of time periods. The monitor determines, based on the predictive model, a set of activities. Each activity corresponds to a different one of the time periods.

The monitor, responsive to determining that a predetermined time threshold has elapsed, generates a log report including, for each of the time periods, the determined activity and displaying the log report on a user interface.

In an further aspect, the monitor receives, over a wireless transceiver, a software update including a new predictive model. The monitor further updates the predictive model with the new predictive model.

In an aspect, an infant monitoring device is configured to determine an activity of an infant. The infant monitoring device includes an inertial measurement sensor and a processor. The processor is configured to perform operations. The operations include receiving, from the inertial measurement sensor, inertial measurements in three dimensions for a time period. The operations include calculating statistical data derived from the inertial measurements. The operations include providing the inertial measurements and the statistical data to a predictive model. The operations include receiving, from the predictive model and based on the inertial measurements, a breathing rate for an infant. The operations include providing the breathing rate to an output device.

In an aspect, the operations further include receiving, from the predictive model, a volume of liquid consumed by the infant during feeding.

In an aspect, the operations further include receiving, from the predictive model, an estimation of (i) a time until a next feeding or (ii) a volume of liquid expected to be consumed at the next feeding.

In an aspect, the inertial measurement sensor can be attached to or removed from an absorbent article.

In an aspect, the inertial measurement sensor is configured to be attached to an absorbent article and not to a body of an infant.

In an aspect, an infant monitoring system includes a monitoring device. The monitoring device includes a first wireless transceiver and a first processor. The first processor is configurable to execute instructions that cause the first processor to perform operations. The operations include receiving an acceleration measurement from the first wireless transceiver of a sensing device. The operations further include providing the acceleration measurement to a predictive model. The operations further include receiving, from the predictive model and based on the acceleration measurement, a determined activity from a predefined activities. The operations further include providing the determined activity to an output device. The sensing device includes an accelerometer configured to sense acceleration in at least one degree of freedom, a second wireless transceiver, and a second processor. The second processor is configured to execute instructions that cause the second processor to receive, from the accelerometer, the acceleration measurement and provide the acceleration measurement to the first wireless transceiver.

In an aspect, the output device is external to the monitoring device. Further, providing the determined activity to an output device includes transmitting the determined activity over a data network connection to the output device.

In an aspect, providing the acceleration measurement to a predictive model includes transmitting the acceleration measurement over a network to a server device. Receiving the determined activity further includes receiving the determined activity over the network from the server device.

In an aspect, the first processor is further configurable to execute instructions that store, in a memory, time series data for a time periods, determining, based on the predictive model, activities, each corresponding to a different one of the time periods; and responsive to determining that a predetermined time threshold has elapsed, generating a log report including the activities and corresponding time periods.

In an aspect, the first processor is further configurable to execute instructions that cause the first processor to transmit, over a data network, the acceleration measurement to a server device configured to log a measurements from an infant monitoring systems.

In an aspect, the predefined activities include (i) awake, (ii) asleep, (iii) stirring, or (iv) settled. In an aspect, the first processor further adjusts the determined activity. For example, when the determined activity is settled, the first processor changes the determined activity to a different state. When the determined activity is stirring, the first processor changes the determined activity to asleep. When the determined activity is (i) asleep, is (ii) below a time threshold, and (iii) occurred during daytime, the first processor changes the determined activity to awake. When the determined activity is (i) awake, is (ii) below a threshold in time, and (iii) occurred during nighttime, the first processor changes the determined activity to asleep.

In a further aspect, the infant monitoring system includes an additional sensor. The first processor is configurable to execute instructions that cause the first processor to perform operations. The operations include receiving, from the additional sensor, an additional measurement of (i) a change in electrical conductivity, (ii) a change in optical properties, (iii) a change in capacitance, (iv) a change in color, or (v) a change in detected volatile organic compound. The operations further include transmitting the additional measurement via the first wireless transceiver to the monitoring device. The sensing device is configurable to execute instructions that cause the second processor to receive, via the second wireless transceiver, the additional measurement from the first wireless transceiver; determine, from the additional measurement, an indication of a presence of (i) urine, or (ii) bowel movement; and provide the indication to the output device.

In an aspect, a wearable device includes a processor, an optical sensor, and an inertial sensor. The optical sensor is configured to obtain a color measurement and transmit the color measurement to the processor. The inertial sensor is configured to detect inertial measurements and provide the inertial measurements to the processor. The processor is configured to perform operations. The operations include receiving the inertial measurements from the inertial measurement sensor. The operations further include providing the inertial measurements to a predictive model. The operations further include receiving, from the predictive model, a determined activity from a predefined activities based on the inertial measurements. The operations further include determining, from the color measurement, an indication of wetness in an absorbent article. The operations further include providing the determined activity and the indication of wetness to an output device.

In an aspect, the wearable device includes a battery operable to power the processor and the inertial measurement sensor.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The patent or application file contains at least one drawing executed in color. Copies of this patent of patent application publication with color drawing(s) will be provided by the Office upon request and payment of the necessary fee. Features, embodiments, and advantages of the present disclosure are better understood when the following Detailed Description is read with reference to the accompanying drawings.

DETAILED DESCRIPTION

Aspects described herein provide solutions for activity classifications systems, specifically activity classification systems designed to detect the movement of an infant and determine whether the infant is performing a specific activity such as sleeping, feeding, nursing, or sitting up.

In an example, an activity classification system includes a movement sensor and an external monitor. The sensor is attached to an infant's clothing or an absorbent article such as a diaper. The sensor, which can include an accelerometer or a gyroscope, provides measurements to the monitor via a wireless communication channel. The monitor is an electronic device that can receive the measurements from the sensor and execute a monitor application and a predictive model such as a machine learning model, state-flow-model, or algorithm to determine activities performed by the infant. In this example, the predictive model is trained to determine, based on the infant's movement, an activity that the infant is performing such as sleep or sitting up. The activity classification system can then indicate to an operator of the monitor the predicted activity of the infant, for example that the infant is in a deep sleep.

Aspects of the present disclosure provide certain advantages over existing solutions. For example, using precise movements gathered from the accelerometer or the gyroscope, the activity classification system can distinguish activities being performed by an infant. For example, the activity classification system can distinguish deep sleep from light sleep, whether the infant is on its stomach versus on its back, or whether the infant is nursing. Further, certain aspects described herein can use predictive models to further refine the system's ability to determine activity. For example, the classification system can distinguish light sleep from deep sleep or measure an infant's breathing rate.

Figure 1:
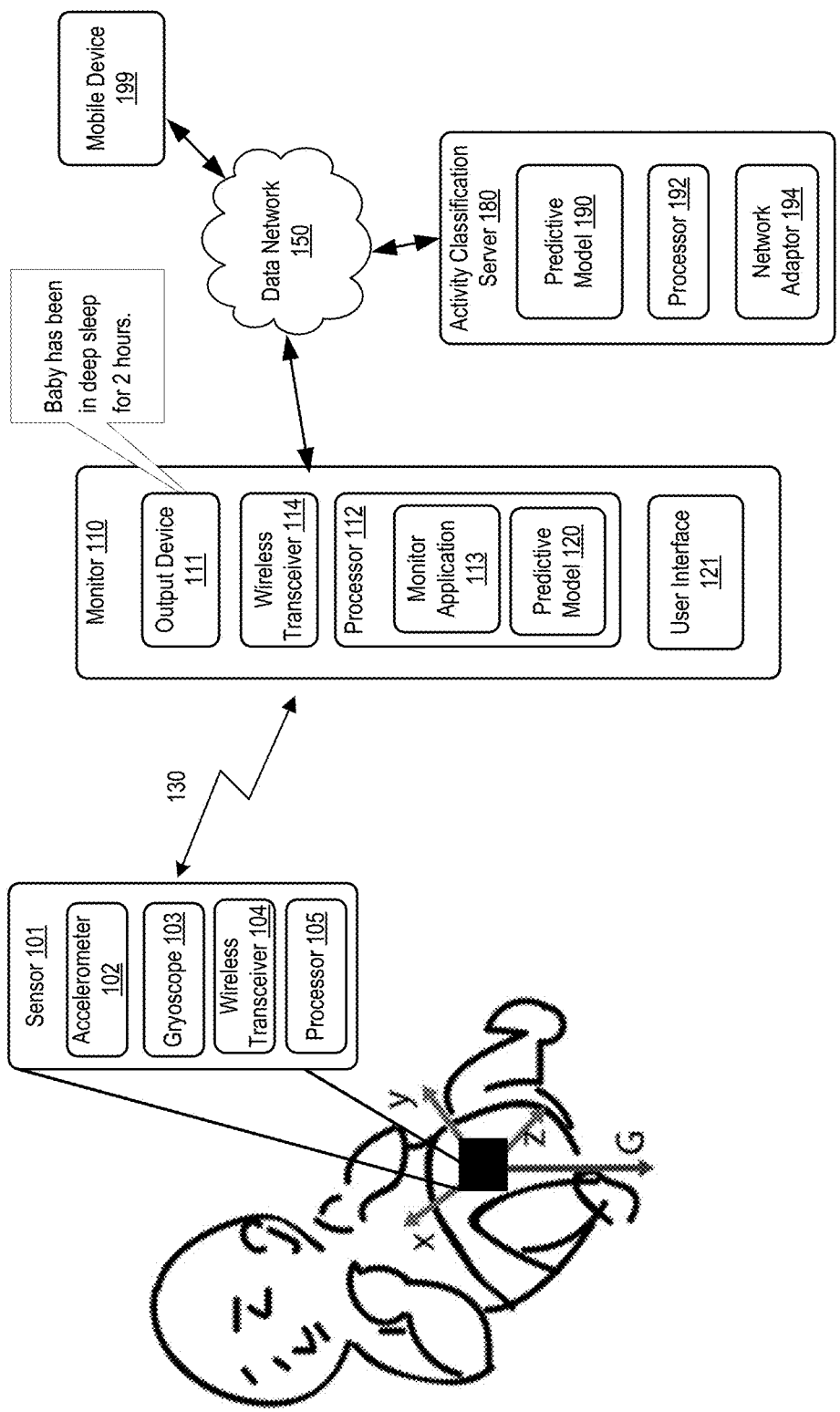
FIG. 1 depicts a block diagram of an activity classification system, according to certain aspects of the present disclosure.

FIG. 1 depicts a block diagram of an activity classification system, according to certain aspects of the present disclosure. Activity classification system 100 includes components that measure the movement of an infant and one or more processors that analyze the measurements to determine the infant's activity. Movement can be determined by inertial measurements, which include acceleration or angular velocity measurements. The one or more processors use an activity function or a predictive model such as a classifier to determine the infant's activity.

Activity classification system 100 includes one or more sensors 101, a monitor 110 connected wirelessly to the sensor 101 via wireless network 130, an activity classification server 180, or mobile device 199.

In an example, monitor 110, which can also be referred to as a hub, can be small enough to be positioned nearby an infant such as on a table or a dresser. Monitor 110 communicates wirelessly with sensor 101, and optionally, with other sensors such as volatile organic compound sensors, urine wetness sensors, noise sensors, light sensors, electrical conductivity sensors, optical sensors, capacitance sensors, color change sensors, and the like. Monitor 110 can aggregate data from sensor 101 or the other sensors.

Monitor 110 can optionally include user interface 121, on which alerts, status information, or other information can be displayed. User interface 121 can include buttons, dials, knobs, a touchscreen, etc. Monitor 110 can communicate over data network 150 to mobile device 199, and cause mobile device 199 to sound alarms, alerts, or provide other information.

In an aspect, user interface 121 can also receive feedback from a user that can help the monitor application 113 better determine when an infant is sleeping. For example, monitor application 113 can ask a user whether an infant is sleeping, and user interface 121 can receive an indication from a user as to whether the infant is actually sleeping. Such information can be incorporated as training data into a predictive model and can help a predictive model become more accurate over time.

In order to measure movement, sensor 101 is positioned on or affixed to a person such as an infant. Sensor 101 includes one or more sensor devices such as an accelerometer 102 or a gyroscope 103. Sensor 101 also includes a wireless transceiver 104 and a processor 105. Sensor 101 gathers measurements of movement and sends the measurements to an external device such as monitor 110. Based on the measurements, monitor 110 can determine the activity being performed by the infant and can take action such as notifying an operator as to what activity the infant is performing.

Securing the sensor 101 can be accomplished in different manners. For example, sensor 101 can be attached to a diaper or an item of clothing. Alternatively, sensor 101 can be pinned or adhered to clothing or an absorbent article or diaper, or fixed in any other way to the infant. Sensor 101 can be attached, removed, and reattached, resulting in the sensor being reusable. Sensor 101 need not touch an infant's skin. Sensor 101 can be inserted into a pouch and removed as necessary. Sensor 101 can be placed anywhere on an infant's body. But as discussed further, placement of the sensor 101 near the infant's waist allows certain advantages such as the ability to determine respiration rate.

To determine movement, processor 105 receives measurements from one or more sensors such as accelerometer 102 and gyroscope 103. Processor 105 transforms the measurements into a form suitable for transmission over wireless network 130, such as by encoding the measurements into a network packet. Processor 105 provides the measurements to wireless transceiver 104, which transmits the measurements to an external device such as monitor 110.

Accelerometer 102 measures acceleration of the infant in one or more dimensions. For example, accelerometer 102 can be a three-dimensional accelerometer that measures acceleration in the x, y, and z directions. In this case, accelerometer 102 provides a triplet of numerical values corresponding to the x, y, and z directions.

Gyroscope 103 measures angular velocity. Gyroscope 103 can output a signal proportional to the angular velocity of the infant. Angular velocity changes in the direction of a torque applied to the gyroscope. Accordingly, when an infant wearing sensor 101 rolls over, gyroscope 103 detects an increase in angular velocity. When the infant stops rolling, the angular velocity returns to zero.

The direction component of the angular velocity can be used in various ways. For example, the direction of the velocity can help indicate which side, e.g., left or right, stomach or back, the infant is positioned. Processor 105 can sample gyroscope 103 at specific instances in time and obtain the angular velocity on a periodic basis.

The accelerometer 102 or gyroscope 103 can provide indications of an infant's activity, breathing rate, or orientation such as on which side an infant is nursing or bottle feeding.

Processor 105 periodically samples accelerometer 102 and/or gyroscope 103 to obtain measurements as needed. Processor 105 provides the sampled measurements to wireless transceiver 104 for transmission to an external device. Processor 105 can sample accelerometer 102 or gyroscope 103 at different rates. For example, processor 105 can use an adaptive sample rate. For example, when the detected level of movement based on the measurements from the accelerometer 102 and the gyroscope 103 are below a threshold, processor 105 can sample less frequently.

A reduction in sample rate can help reducing power consumption by disabling devices such as the wireless transceiver 104 or entering into and remain in a low power state. Processor 105 can also perform additional processing or analysis on the measurements before providing the measurements to wireless transceiver 104. For example, processor 105 may only provide measurements via wireless transceiver 104 to an external device when the measurements indicate a threshold level of activity. In this manner, processor 105 can save power by not causing the wireless transceiver 104 to transmit data. Conversely, when the measurements indicate activity above a second threshold, processor 105 can sample the accelerometer 102 and gyroscope 103 more frequently. In this manner, processor 105 can obtain more detailed measurements during bursts of activity.

The processor 105 transmits the measurements to an external device such as monitor 110 using the wireless transceiver 104. In some examples, the processor 105 can transmit measurements to the external device, e.g., the monitor 110, as they are received from the accelerometer 102 and gyroscope 103, or in some examples it can buffer the measurements and send a group of measurements to the monitor 110 all at once.

The wireless transceiver 104 is configured to send and receive radio communications to enable communications between the sensor 101 and one or more external devices, such as monitor 110. The wireless transceiver 104 can provide wireless communications using any suitable wireless protocol such as Bluetooth or WiFi to transmit data or other information, such as a measurement of acceleration from accelerometer 102 or a measurement of angular velocity, to the monitor 110. In some examples, the wireless transceiver 104 can also transmit other information, such as a status message that indicates whether the sensor 101 is operational, in a stand-by mode, or deactivated. In an aspect, wireless transceiver 104 can receive radio transmissions from an external device. For example, wireless transceiver can receive information and commands from monitor 110. For example, monitor 110 can send a message to wireless transceiver 104 that causes the sensor 101 to turn on, enter a low power state, or turn off.

In this example, monitor 110 includes output device 111, processor 112, monitor application 113, wireless transceiver 114, and predictive model 120. Monitor 110 operates in conjunction with sensor 101 and optionally activity classification server 180 to determine an activity being performed by the infant. To do so, the monitor 110 receives sensor measurements such as acceleration and angular velocity from sensor 101 and uses the monitor application 113 in conjunction with the predictive model 120 to determine an activity based on the received sensor measurements. In this example, the predictive model 120 is a state-machine or algorithm, but may be any suitable type of predictive model in different examples such as a machine learning model or a classification model.

Wireless transceiver 114 can send and receive messages via a wireless protocol such as Bluetooth, WiFi, or any other wireless protocol. To enable wireless communications in this example, the wireless transceiver 114 can be paired with a sensor device such as sensor 101. Wireless transceiver 114 receives sensor data from wireless transceiver 104 obtained from accelerometer 102 or gyroscope 103.

Monitor 110 uses the measurements to determine an activity being performed by the infant. For example, monitor 110 can apply the measurements to the predictive model 120, which can determine whether an infant wearing sensor 101 is feeding on the left hand side, feeding on the right hand side, sleeping, awake and playing on its back, being held, sitting, or performing some other activity.

Based on the determined activity, monitor 110 can take action. For example, monitor 110 can display a message to an operator or sound an alert or it can use output device 111 to alert an operator of monitor 110 about an activity, such as whether an infant wearing the sensor 101 is awake or asleep.

Output device 111 can be a display such as an LCD or LED display, touchscreen display, light, flashing light, speaker, or other output device.

In an aspect, predictive model 120 can determine the breathing rate of the infant. For example, if the sensor 101 is placed on the infant's waist or stomach, then the infant's breathing will cause the sensor to move back and forth in one direction causing the sensor to output one or more sensor signals indicating the movement. Monitor application 113 can determine the infant's frequency of breathing from the measurement of activity. Monitor application 113 can also use the activity levels to distinguish a small fall from a large fall, for example, a fall that requires intervention. Similarly, monitor application 113 can determine when the infant's heart is beating and thereby determine the heartrate of the infant. Heartrate and breathing rate can be used to help determine when the infant is in different stages of sleep such as light sleep, deep sleep, about to wake up, etc. Heart rate, or the differences between resting heart rate and active heart rate, can also indicate the infant's health such as whether the infant has a fever.

In a further aspect, predictive model 120 can determine future activities from past activities. For example, predictive model 120 can be trained to recognize trends such as a time series of sensor values that indicate deep sleep for a period of time followed by increasing levels of movement. Such a trend in the time series of acceleration data can indicate that an infant is waking up.

In an aspect, the monitor 110 can use the wireless transceiver 114 to connect via data network 150 to an activity classification server 180. Data network 150 can be a local network, the Internet, or both. For example, wireless transceiver 114 can wirelessly to activity classification server 180 or mobile device 199.

Activity classification server 180 can be configured to perform additional analysis such as population-level analysis of the movements of multiple infants or training of one or more predictive models and providing predictive models to the monitor 110.

Activity classification server 180 includes predictive model 190, processor 192, and network adaptor 194. Network connectivity from the monitor 110 to an activity classification server 180 provides several advantages. For example, via data network 150, monitor 110 can receive software updates from a vendor or transmit status information to the vendor. Software updates can include updates to predictive model 120.

Predictive model 190 can be a machine learning model such as a decision tree classifier or a regression model. Predictive model 190 can be trained to perform similar functions as predictive model 120. For example, predictive model 120 can be trained to determine whether a wearer of the sensor is feeding on the left hand side, feeding on the right hand side, sleeping, awake and playing on its back, being held, or sitting. In particular, movement detected by gyroscope 103 is useful to predict feeding.

Updates to the predictive models are possible. For example, predictive model 190 can also update predictive model 120. For example, as explained further herein, predictive model 190 can be trained using data from multiple monitors 110a-n. In this manner, predictive model 190 can become more accurate because it has been trained on a larger data set than might be available from only one monitor. Updating predictive model 120 with the training of predictive model 190 provides each monitor 110a-n the ability to benefit from population-based training.

Network adaptor 194 connects to a data network such as data network 150. In this manner, network adaptor 194 can communicate with monitor 110 via wireless transceiver 114. Network adaptor 194 can therefore receive updates such as new training data gathered from monitor 110. Network adaptor 194 can also provide updated software or trained predictive models to monitor 110.

Processor 192 is processor that receives data from network adaptor 194. over data network 150. Processor can be a processor such as processor 2102 described in FIG. 20. Processor 192 can perform similar operations as processor 112. For example, processor 192 can execute an application such as monitor application 113. Such an application can train a predictive model such as predictive model 190, receive measurement data over data network 150, and use predictive model 190 to determine the activity of an infant.

Mobile device 199 can be a smart phone, tablet, laptop, or other device. Mobile device 199 can include a graphical user interface that outputs data such as how long an infant has slept, a predicted nursing time, etc., as further depicted in FIGS. 10-14. Mobile device 199 can send alerts to an operator such as an indication that the infant as woken up, fallen asleep, is crying, etc. Mobile device 199 can communicate with monitor 110 or activity classification server 180 over data network 150. Mobile device 199 can include perform some or all of the processing handled by processors 105, 112, or 192.

Sensor 101, monitor 110, and activity classification server 180 operate in conjunction with each other to determine an infant's activity. Processing of the measurement data and determination of the infant's activity can be performed on sensor 101, e.g. via processor 105, monitor 110, e.g. via processor 112, or activity classification server 180, e.g., via processor 192.

For example, processor 105 can receive the measurements such as acceleration and angular velocity and sensor 101 can provide the unmodified measurement data to monitor 110 across wireless network 130. In turn, processor 112 receives the measurements from sensor 101 via wireless transceiver 114. Processor 112, for example via monitor application 113, uses an activity function to determine the activity of the infant.

Alternatively, processor 105 can derive an activity function from the acceleration and angular velocity measurements. Processor 105 provides the activity function to the wireless transceiver 104. Processor 112 receives the activity measurement function data and makes a prediction of the infant's activity.

In a further aspect, monitor 110 can also provide the measurements from sensor 101, via data network 150, to activity classification server 180, which can determine the infant's activity. Activity classification server 180 may provide additional processing resources, resulting in a more accurate prediction of the infant's activity, or it may update its predictive model 190 based on the received measurements.

In an aspect, activity classification server 180 connects to multiple activity monitors 110 and aggregates measurement data or determines activities for multiple infants. Activity classification server 180 can analyze the data for trends. Trends that are difficult to discern can be easier to discern using multiple sets of data. For example, in conjunction with demographic information such as the age of the infants being measured, activity classification server 180 can determine the average amount of sleep received by an infant of a certain age.

Activity classification server 180 can also aggregate training data from multiple infants and improve the training of predictive model 190. Predictive model 190 can be deployed into the predictive model 120 of each monitor 110.

Figure 2:
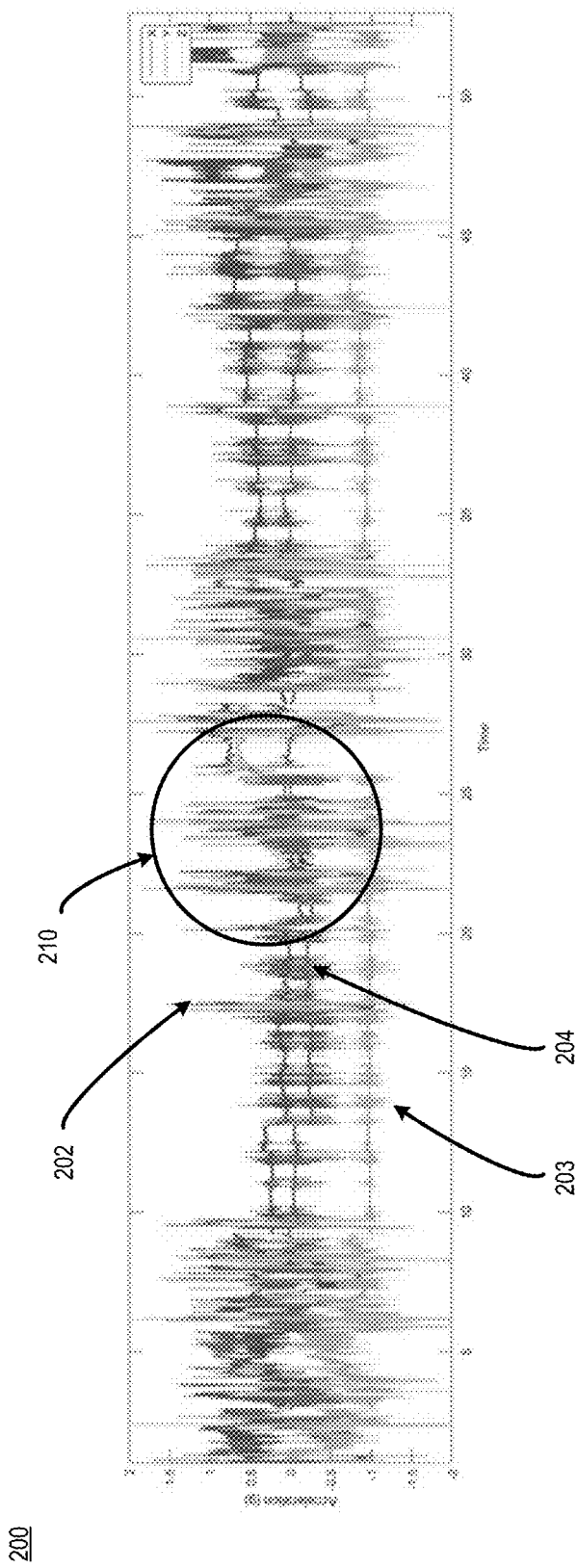
FIG. 2 depicts examples of sensor outputs from an accelerometer, according to certain aspects of the current disclosure.

FIG. 2 depicts examples of sensor outputs from an accelerometer, according to certain aspects of the current disclosure. FIG. 2 includes graph 200, which includes waveforms 202, 203 and 204. Waveform 202 represents a measurement of activity in the x dimension of sensor 101, waveform 203 represents a measurement of activity in the y dimension of sensor 101, and waveform 204 represents a measurement of activity in the z dimension of sensor 101. Graph 200 includes a vertical axis that indicates acceleration (g), and a horizontal axis that indicates time (hours).

As can be seen in graph 200, bursts of activity, shown as higher values, are present such as burst 210, which correlates with movement detected by sensor 101. A burst of activity may occurs when the infant moves in some way that causes one or more sensors to output sensor signals indicating, for example, acceleration. For example, when the infant rolls over, a burst of activity is detected because one or more accelerometers output sensor signals indicating accelerations that are more than a threshold value away from zero acceleration, or an angular velocity in the direction of the roll (not shown in FIG. 2) that is more than a threshold value away from zero angular velocity. Similarly, when the infant is resting, the infant's breathing can appear as bursts of activity at the breathing rate. In contrast, during periods without bursts of activity, the infant is either not moving or moving very little. As explained further, monitor application 113 can distinguish between movements using an activity function or a predictive model 120.

Figure 3:
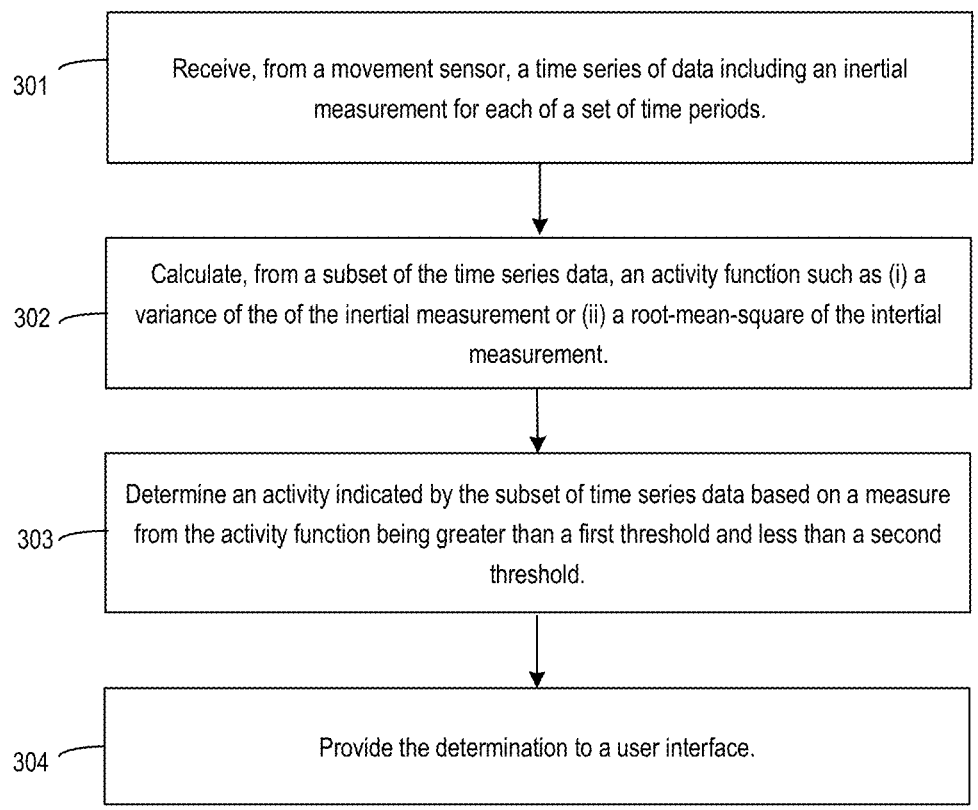
FIG. 3 is a flowchart of an exemplary method used to determine activity from movement sensors, according to certain aspects of the present disclosure.

FIG. 3 is a flowchart of an exemplary method used to determine activity from movement sensors, according to certain aspects of the present disclosure. For example purposes, method 300 is illustrated with respect to monitor application 113. But method 300 can be performed by software executing on a processor such as processor 192 of a remote device such as activity classification server 180.

At block 301, monitor application 113 receives, from a movement sensor, a time series of data including an inertial measurement for each of a set of time periods. Inertial measurements can include acceleration or angular velocity. For example, accelerometer 102 provides a triplet of numerical values corresponding to the x, y, and z directions to processor 105, which provides the triplet to wireless transceiver 104. Processor 105 periodically samples accelerometer 102 to create a time series of data. Processor 105 annotates each triplet with a timestamp, creating a pair that includes sensor measurement and timestamp. Processor 105 can also sample gyroscope 103 on a periodic basis. In conjunction with the measurement data from accelerometer 102, processor 105 can provide a set of data to monitor 110. The set of data can include a gyroscope measurement, e.g. angular velocity, an accelerometer measurement, e.g., a triplet of x-y-z values, and a timestamp.

In an aspect, activity classification system 100 analyzes measurement data in real-time. For example, processor 105 can cause wireless transceiver 104 to transmit each sampled triplet and timestamp pair separately to monitor 110 in real-time. In this manner, monitor application 113 can update an activity measurement function or predictive model 120 in real-time.

Alternatively, activity classification system 100 can analyze a block of samples at a time. For example, processor 105 can buffer the pairs until a threshold number of pairs have been received, then transmit a batch consisting of all the pairs gathered to monitor 110. Processor 105 can also buffer the pairs until a threshold amount of time has passed, then provide the pairs to monitor 110. In this manner, processor 105 can analyze movement over different windows of time.

Other types of movement sensors can be used such as vibration sensors, ultrasonic sensors, or passive infrared sensors. Such sensors can have single or multiple dimensions. Processor 105 can sample such sensors and create a set of data containing sensor values and timestamp to send to monitor 110.

At block 302, monitor application 113 calculates, from a subset of the time series of data, an activity function from statistical data derived from the inertial measurement. Statistical data can include data such as (i) a statistical variance of the inertial measurement or (ii) a root-mean-square of the inertial measurement. Monitor application 113 uses an activity measurement function in order to determine activity level. Different measurements of activity can be derived. For example, monitor application 113 can calculate the statistical variance, standard deviation, or the root mean square (RMS) of the signal. Monitor application 113 can use another customized metrics based on the accelerometer or gyroscope data. For example, a customized metric that quantifies the level of activity A can be calculated for a given number n of samples with the following function, where Sx, Sy, and Sz are the sum of the square differences from the respective means in the x, y, and z dimensions respectively:

$$A = \sqrt{\frac{(Sx)^2 + (Sy)^2 + (Sz)^2}{n}}$$

At block 303, monitor application 113, determines an activity indicated by the subset of time series data based on a measure from the activity function being greater than a first threshold and less than a second threshold. Monitor application 113 can determine an activity such as sleeping or awake based on a level of activity being with a range of values. For example, if the activity function measures a level of activity below a first threshold but above zero, then the monitor application 113 determines that the infant is in light sleep. If the activity function measures a level of movement below a second, lower, threshold, then the monitor application determines that the infant is in a deep sleep. As discussed further with respect to FIG. 10, monitor application 113 can use a state machine to determine activity states.

At block 304, monitor application 113 provides the activity to a user interface. For example, the monitor application 113 can output the activity such as "deep sleep" or "light sleep," for example, by providing an silent alert to output device 111 to indicate to a caregiver that the infant is asleep. The monitor application 113 can also log the activity and a timestamp in a memory and provide the logged information to activity classification server 180.

Monitor application 113 can also output information derived from the activity of the infant. For example, output device 111 can provide an indication to the operator such as "the baby has been asleep for two hours." Monitor application 113 can also cause a sound such as an alert from output device 111, for example, when the infant has woken up after being asleep for a predetermined amount of time. Monitor application 113 can also transmit information to a remote device, such as activity classification server 180. In this manner, the activity classification system 100 can be useful for caregivers of multiple infants, for example, at a hospital or a daycare.

As discussed, in an aspect, activity classification system 100 can use a predictive model such as predictive model 120 or predictive model 190 to determine the infant's activity in addition to or instead of algorithms or state machines. Monitor application 113 provides the accelerometer measurements, the gyroscope measurements, or the output of an activity measurement function to the predictive model 120, or both.

Predictive models discussed herein can be machine learning models such as decision tree classifier or regression models. Other models are possible. Predictive model 120 is trained to determine whether a wearer of the sensor is feeding on the left hand side, feeding on the right hand side, sleeping, awake and playing on its back, being held, or sitting. Other detectable activities may include sitting, playing, crawling, walking, etc. Monitor application 113 provides data for one or more periods of time to predictive model 120. In this manner, predictive model 120 may therefore determine an activity based on present or past activity level.

Predictive model 120 can be updated or upgraded, for example, via a data network 150. As discussed further herein, predictive model 120 can also be trained locally on the monitor 110. For example, an operator such as a parent can indicate to the monitor 110 that the wearer of the sensor was asleep or awake during a particular time period. The monitor application 113 can then update predictive model 120 based on the additional information provided.

Figure 4:
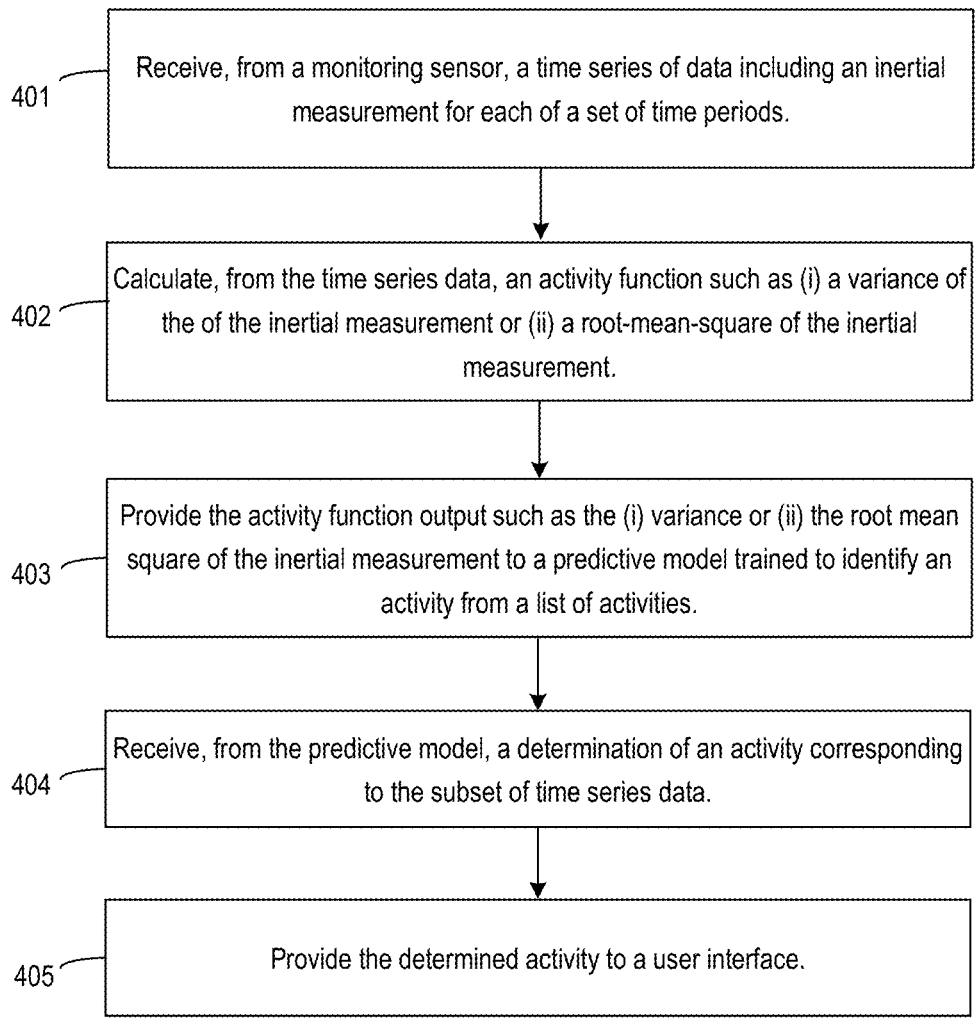
FIG. 4 is a flowchart of an exemplary method used to determine activity from a movement sensor by using a predictive model, according to certain aspects of the present disclosure.

FIG. 4 is a flowchart of an exemplary method used to determine activity from a movement sensor by using a predictive model, according to certain aspects of the present disclosure. For example purposes, method 400 is illustrated with respect to monitor application 113 and predictive model 120. But activity classification server 180 and predictive model 190 can also perform method 400.

At block 401 of method 400, monitor application 113 receives, from a movement sensor, a time series of data including an inertial measurement for each of a set of time periods. At block 401, monitor application 113 receives the time series of data generally as described with respect to block 301.

At block 402 of method 400, monitor application 113 calculates, from the time series data, an activity function such as (i) a statistical variance of the of the inertial measurement or (ii) a root-mean-square of the inertial measurement. At block 402, monitor application uses an activity measurement function generally as described with respect to block 302.

At block 403 of method 400, monitor application 113 provides the activity function the (i) statistical variance or (ii) the root mean square of the inertial measurement to a predictive model trained to identify an activity a list of activities. More specifically, monitor application 113 provides sensor measurements or the output of the activity function to the predictive model 120.

Predictive model 120 is trained to determine activity from measurements that indicate movement. The predictive model 120 determines, based on its training, from a predefined set of classes, to which class the activity belongs. An exemplary list of activity classes includes feeding on the left side, feeding on the right side, sleeping, awake but playing on back, being held, and sitting.

Other training classes are possible. For example, predictive model 120 can be trained to distinguish deep sleep from light sleep, and activities such as crawling, rolling, sitting up, feeding, or nursing from each other. For example, monitor 110 may include a predictive model that is trained to distinguish between asleep, awake, stirring, or settled states, and another that is trained to distinguish between light sleep and deep sleep. Training is discussed further with respect to FIG. 9. Stirring represents a state in which an infant is moving more than a first threshold amount and settled represents a state in which the infant has calmed down and is moving less than a second threshold amount.

At block 404 of method 400, monitor application 113 receives, from the predictive model, a determination of an activity corresponding to the subset of time series data. For example, predictive model 120 provides a prediction to monitor application 113 from one of the trained categories such as feeding on the left hand side, feeding on the right hand side, sleeping, awake and playing on its back, being held, or sitting. An illustration of activities determined by the predictive model is shown in FIG. 5.

Figure 5:
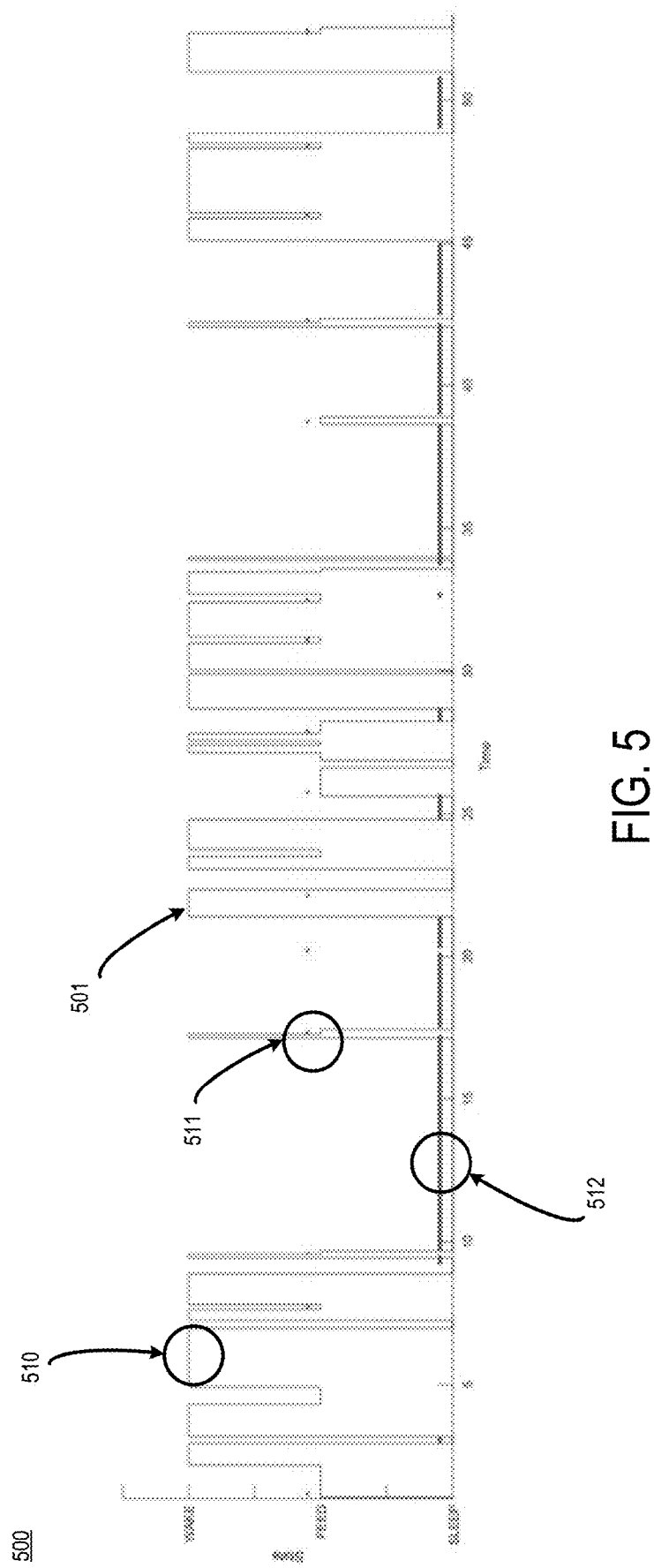
FIG. 5 depicts a graph that shows activities determined by a predictive model based on movement detected from an accelerometer, according to certain aspects of the present disclosure.

FIG. 5 depicts a graph 500 that shows activities determined by a predictive model based on movement detected from an accelerometer and a gyroscope, according to certain aspects of the present disclosure. Graph 500 includes waveform 501, Wake state 510, Feed state 511, and Sleep state 512. Graph 500 indicates activities that were determined based on the sensor information shown in graph 200 of FIG. 2.

Waveform 501 represents an output from a predictive model such as predictive model 120 over time. In the aspect depicted by graph 500, predictive model 120 is trained to determine one of three activities: wake, feed, or sleep. Graph 500 includes wake state 510 corresponding to waking up, feed state 511 corresponding to feeding or nursing, and sleep state 512 corresponding to sleeping. Accordingly, at a given point in time, the output represented by waveform 501 is in one of states 510-512.

In graph 500, the units of time are hours. Therefore, as can be seen, predictive model 120 has predicted that the infant has slept for various periods of time from a few hours to seven or more hours. The dots indicated by feed state 511 represent feeding, which indicates typical feeding times of 20-30 minutes measured by the predictive model.

States 510-512 can also represent annotated training information provided to the predictive model 120. For example, data that indicates the infant's activity can be obtained via monitor 110 or another device and provided with the predicted states and a prompt for user input. For example, monitor 110 can prompt an operator such as a caregiver with a prompt such as "the monitor has determined the baby is asleep. True or false?"

Returning to FIG. 4, at block 405 of method 400, at block 405 of method 400, monitor application 113 provides the determined activity to a user interface. At block 405, the monitor application 113 outputs the activity generally as described with respect to block 304.

As discussed, predictive models such as predictive model 120 or predictive model 190 can be trained before use. Predictive model 120 can be trained with supervised or unsupervised learning. With supervised learning, the predictive model is provided annotated or labeled training data that indicates the actual activity of the infant, such as whether the infant is asleep, awake, or feeding. The training data is provided to the predictive model, which creates a loss function and compares the loss function to the actual, annotated or labeled, value.

In an aspect, additional training can be performed locally by an operator of monitor application 113. For example, training data can be augmented at runtime by the device such as a caregiver. For example, monitor 110 can prompt the operator "the activity monitor thinks your baby is sleeping, is that correct?" In this manner, the predictive model 120 can be continuously updated and improved over time. Predictive model 120 can be tailored to one specific infant's tendencies. For example, one infant may sleep lighter than another, causing a prediction for one infant to require adjustment for use with a second infant.

Figure 6:
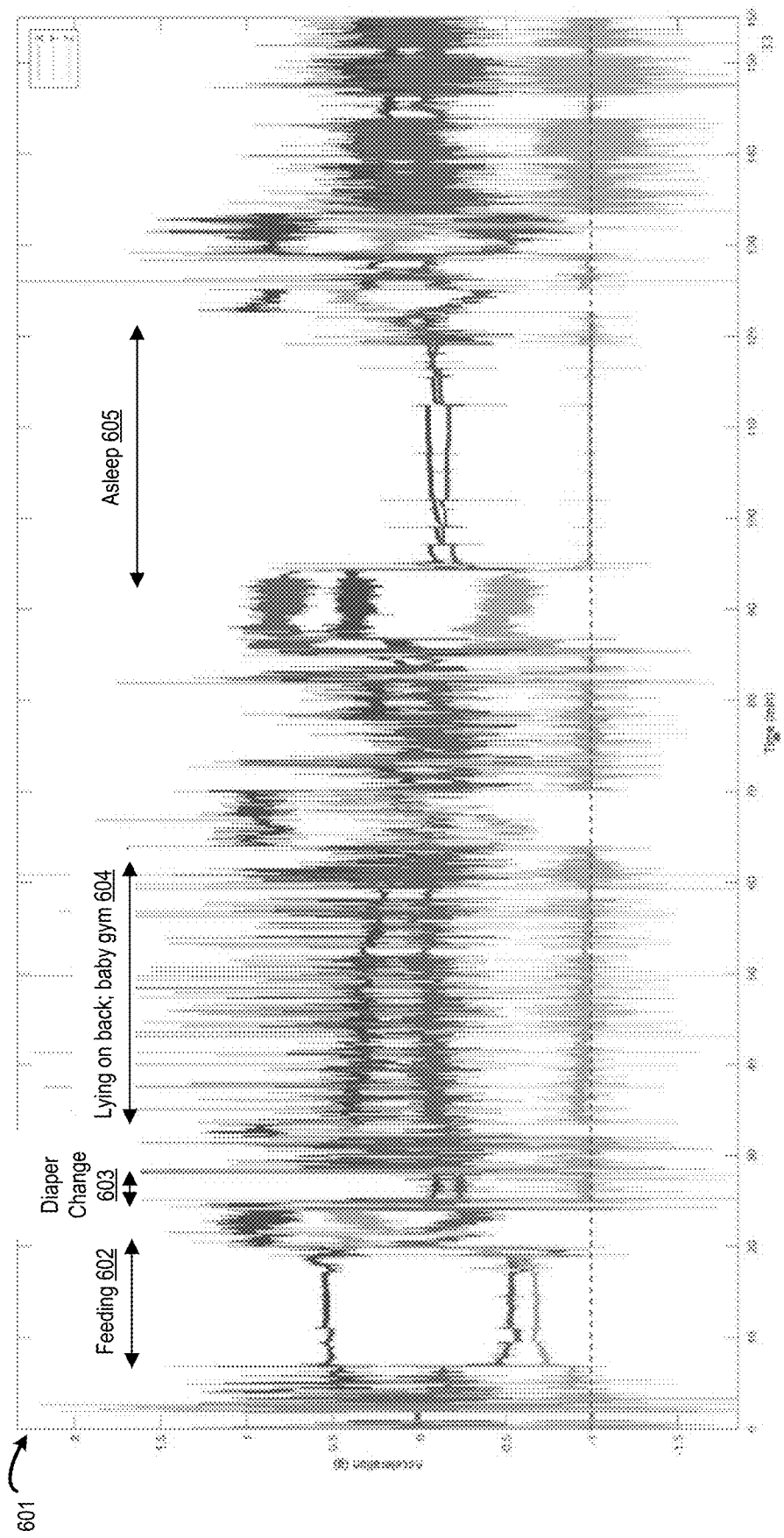
FIG. 6 depicts examples of sensor outputs from an accelerometer annotated with predicted states, according to certain aspects of the present disclosure.

FIG. 6 depicts examples of sensor outputs from an accelerometer annotated with predicted states, according to certain aspects of the present disclosure. FIG. 6 includes graph 601. Graph 601 shows accelerometer outputs on the x, y, and z axes for a sensor attached to an infant subject. Graph 601 is annotated with identified, or predicted activity states 602, 603, 604, and 605. Activity state 602 represents a state in which the infant is feeding. As can be seen, movement as detected by the accelerometer is relatively small compared to other states such as 604, which represents a time at which the infant is lying on its back and playing with the baby gym. Activity state 603 represents a diaper change. State 605, which as can be seen, shows relatively little to no movement, depicts when the infant is sleeping. Aspects described herein can be trained to predict activity states such as those depicted by 602-605, and others such as lying on stomach, lying on side, etc.

Figure 7:
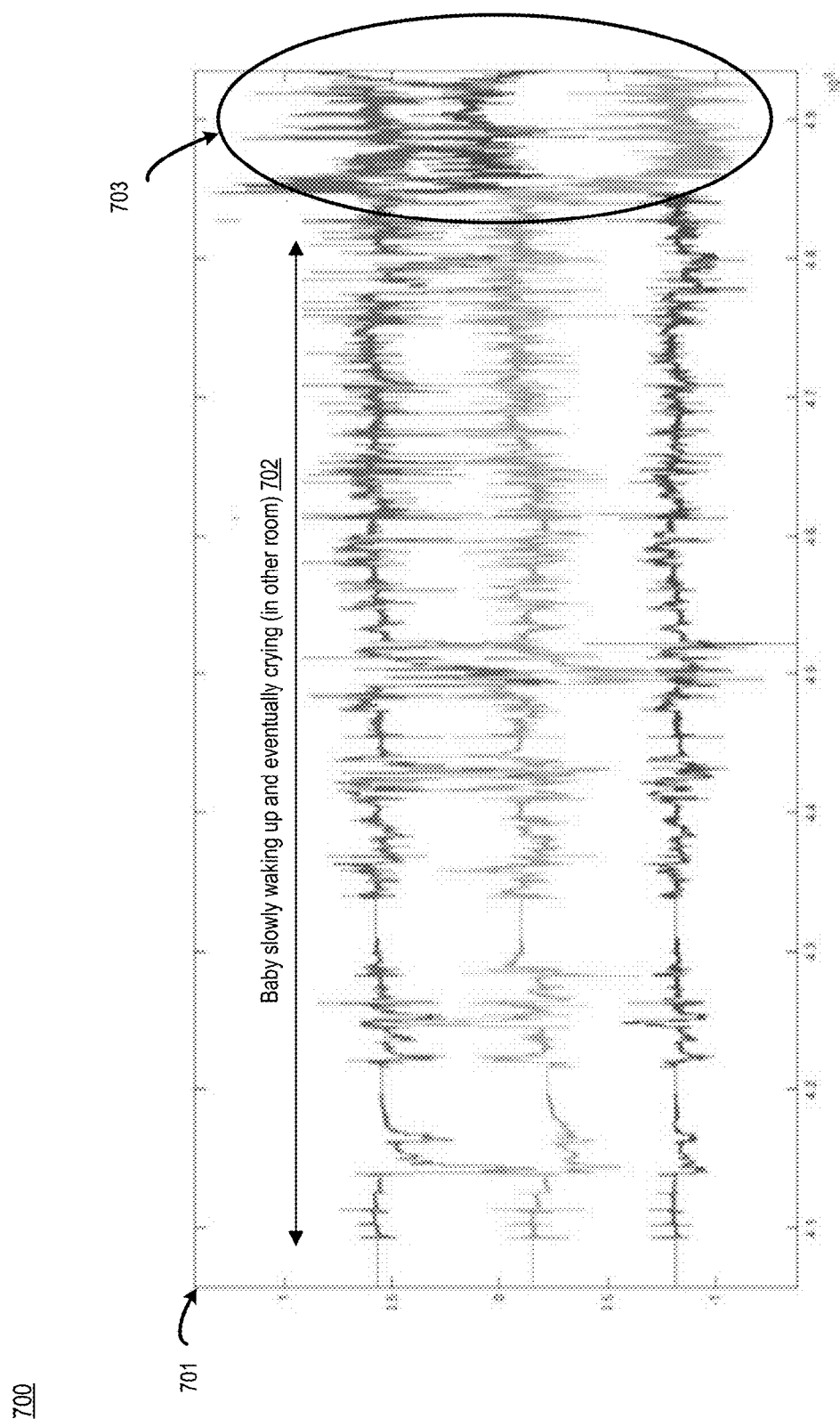
FIG. 7 depicts examples of sensor outputs from an accelerometer that indicate sleep and waking up according to certain aspects of the present disclosure.

FIG. 7 depicts examples of sensor outputs from an accelerometer that indicate sleep and waking up according to certain aspects of the present disclosure. FIG. 7 includes graph 701, which depicts activity states 702 and 703. Activity state 702 indicates data that represents an infant subject in the process of slowly waking up and building up to eventually crying. Activity state 703 represents that the infant is awake. Aspects described herein can be trained to distinguish between activity states 702 and 703.

Figure 8:
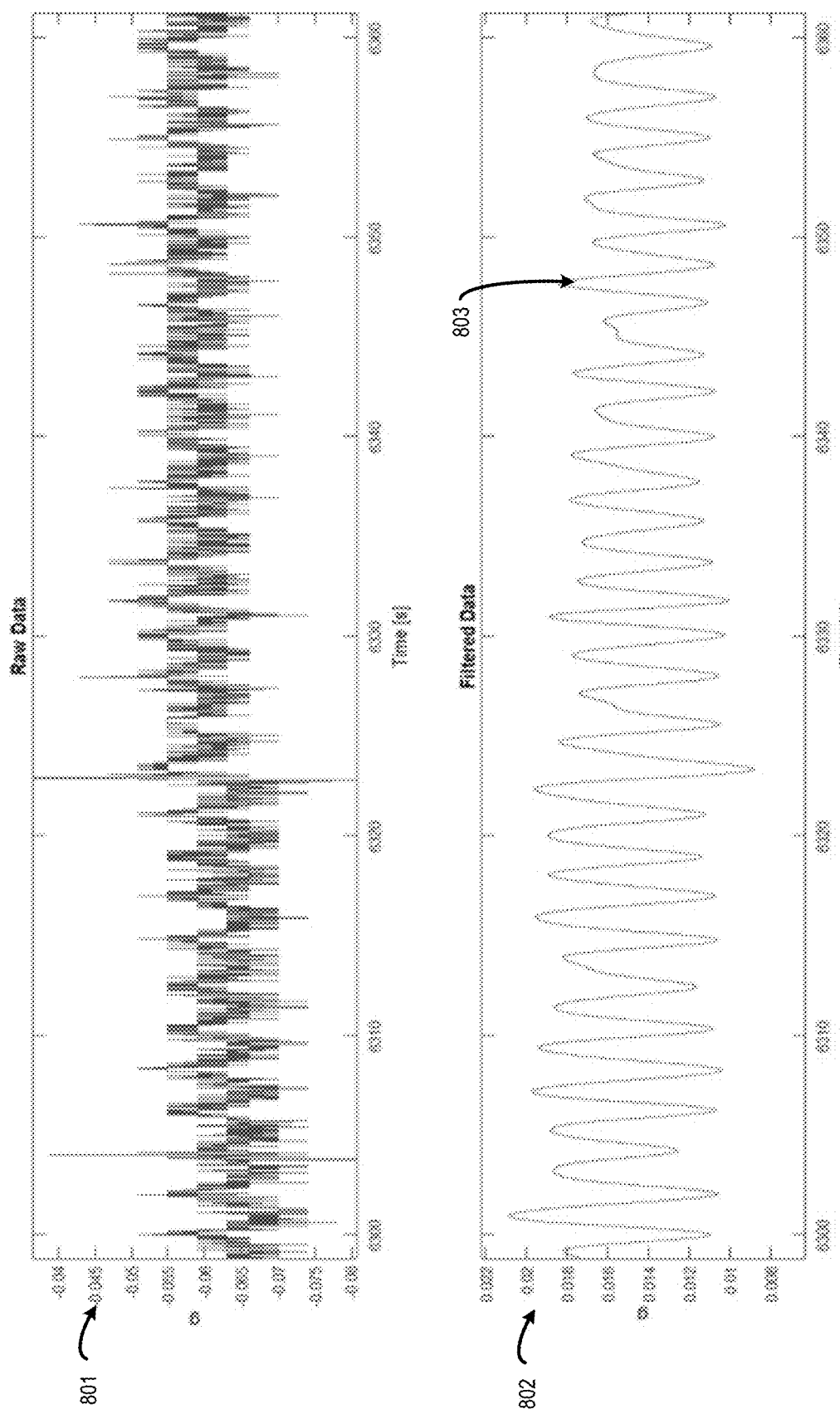
FIG. 8 depicts examples of sensor outputs that indicate a detected respiratory rate of an infant, according to certain aspects of the present disclosure.

FIG. 8 depicts examples of sensor outputs that indicate a detected respiratory rate of an infant, according to certain aspects of the present disclosure. When an infant subject is asleep, the accelerometer can detect small movements in one or more directions that vary based on a frequency and identify those movements as respiration. FIG. 8 includes graphs 801 and 802. Graph 801 depicts a waveform that correlates with breathing rate. Graph 802 depicts a waveform derived from the waveform in graph 801, but filtered by a band-pass filter, e.g., that allows 0.1-1 Hz frequencies to pass. As can be seen, the waveform 803 is easy to discern. Waveform 803 illustrates a breathing frequency of approximately 28 breaths per minute.

Figure 9:
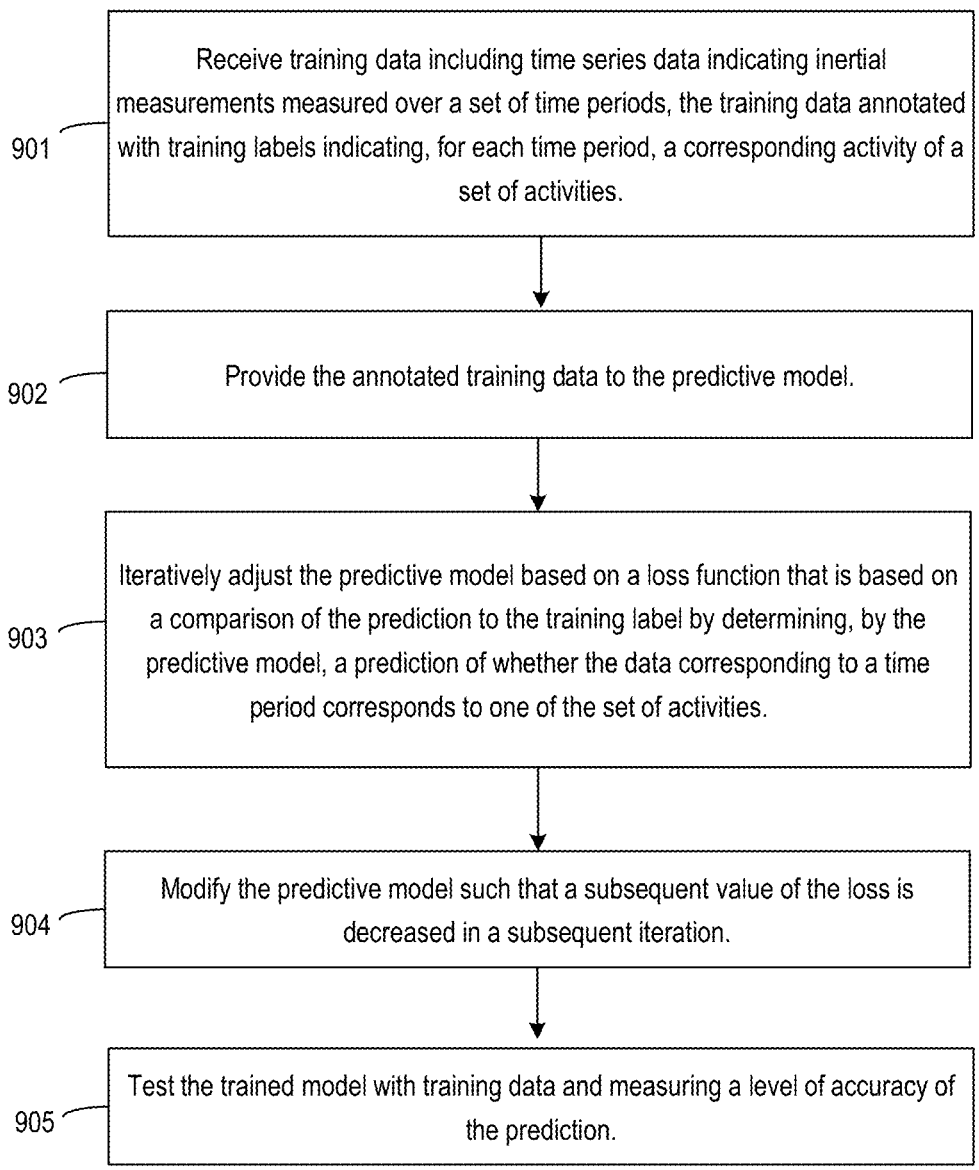
FIG. 9 is a flowchart of an exemplary method for training a predictive model to determine activity from movement, according to certain aspects of the present disclosure.

FIG. 9 is a flowchart of an exemplary method for training a predictive model to determine activity from an infant's movement, according to certain aspects of the present disclosure. Predictive model 120 can be trained by monitor application 113 executing on monitor 110, or a computing system such as computing system 2100 depicted in FIG. 21. Similarly, an external device such as activity classification server 180 can train predictive model 190 using method 900.

At block 901, monitor application 113 receives training data including time series data indicating inertial measurements measured over a set of time periods, the training data annotated with training labels indicating, for each time period, a corresponding activity of a plurality of activities. In some cases, the training data labels are provided by a caregiver. For example, a caregiver can indicate what an infant was doing at a particular time, and monitor application 113 can combine the indication with the accelerometer or gyroscope data to provide training data to train one of the predictive models.

For example, the training data consists of multiple instances of training data. Each instance includes a measurement of movement. A measurement of movement includes acceleration, e.g., an x-y-z triple, or a measure of angular velocity from a gyroscope. Each instance therefore represents a snapshot in time of movement.

The training data is annotated with labels that correspond to real, measured activity such as whether an infant was asleep or awake. For example, each instance of training data is annotated with a label that indicates an actual determined activity of an infant, specifically, the activity that an infant was performing at the time that corresponds to that instance of training data, e.g., when the measurements were taken.

In an aspect, training data can include instances that represent a time period. For example, an instance can represent a period of one second. Accordingly, the instance may include multiple samples of movement data with one associated activity annotation.

At block 902, monitor application 113 provides the annotated training data to the predictive model. Monitor application 113 provides one instance of training data to the predictive model 120 at a time.

At block 903, monitor application 113 iteratively adjusts the predictive model based on a loss function that is based on a comparison of the prediction to the training label by determining, by the predictive model, a prediction of whether the data corresponding to a time period corresponds to one of the plurality of activities.

Specifically, the predictive model 120 outputs an activity from a predefined set of activities. A set of activities could be, for example, feeding on the left side, feeding on the right side, sleeping, awake but playing on back, being held, and sitting. The loss function is a comparison of the predicted activity, e.g., what activity determined by the predictive model to correspond to the time series data, with the activity as indicated by the training label. The predicted activities can be represented numerically or in another fashion.

At block 904, monitor application 113, reduces the value of a loss function based on a comparison of the determined activity from the predictive model and the labeled activity. The loss function computes the difference between the determined activity and the labeled activity, e.g., the activity that the infant who was the subject of the training data was actually performing at that time. Predictive model 120 attempts to minimize the loss function with each iteration and adjusts its internal parameters accordingly.

Monitor application 113 repeats steps 902-904 with subsequent instances of training data. Predictive model continues to update and reduce the value of the loss function over each iteration.

After a sufficient amount of training data, the predictive model learns to distinguish sleeping from not sleeping. For example, after a sufficient number of examples of deep sleep and light sleep, predictive model can learn to distinguish deep sleep from light sleep. Other training examples include distinguishing when an infant is in its belly versus on its back, and whether the infant is nursing and if so, on which breast. The orientation of the infant is useful for distinguishing breastfeeding, bottle feeding, and eating solid food. For example, certain orientations such as completely vertical or completely horizontal are less likely than other orientation.

At block 905, a monitor application 113 tests the trained model with a set of test data that is separate from the training data and measures a level of accuracy of the prediction. The test data is separate from the training data that is used for training purposes as described with respect to blocks 901-904. The test data is not provided to the predictive model 120 until testing. In this manner, the test data is new to the predictive model 120 and therefore cannot influence the model's prediction. The test data therefore can be used to rigorously test whether the training has worked. If the predictive model fails a threshold number of tests, then the model is further trained.

In an aspect, activity classification system 100 can be integrated with a system that can measure urine in a diaper, temperature, humidity, bowel movements of the infant, or other data. For example, an integrated sensor can include sensor 101, e.g., accelerometer 102 and gyroscope 103, and additional sensors such as temperature, humidity, and the like. Sensor 101, specifically processor 105, can transmit additional measurements such as temperature measurements and humidity measurements to monitor 110. In turn, monitor application 113 can then determine when the infant's diaper needs to be changed and provide an alert, for example, via output device 111. In a further aspect, monitor 110 can receive data transmitted from a sensor that measures the color of a color strip. The monitor 110 can detect, by the color of the color strip, a volume of urine present in the infant's diaper. Monitor 110 can output an alert to a caregiver via output device 111.

Figure 10:
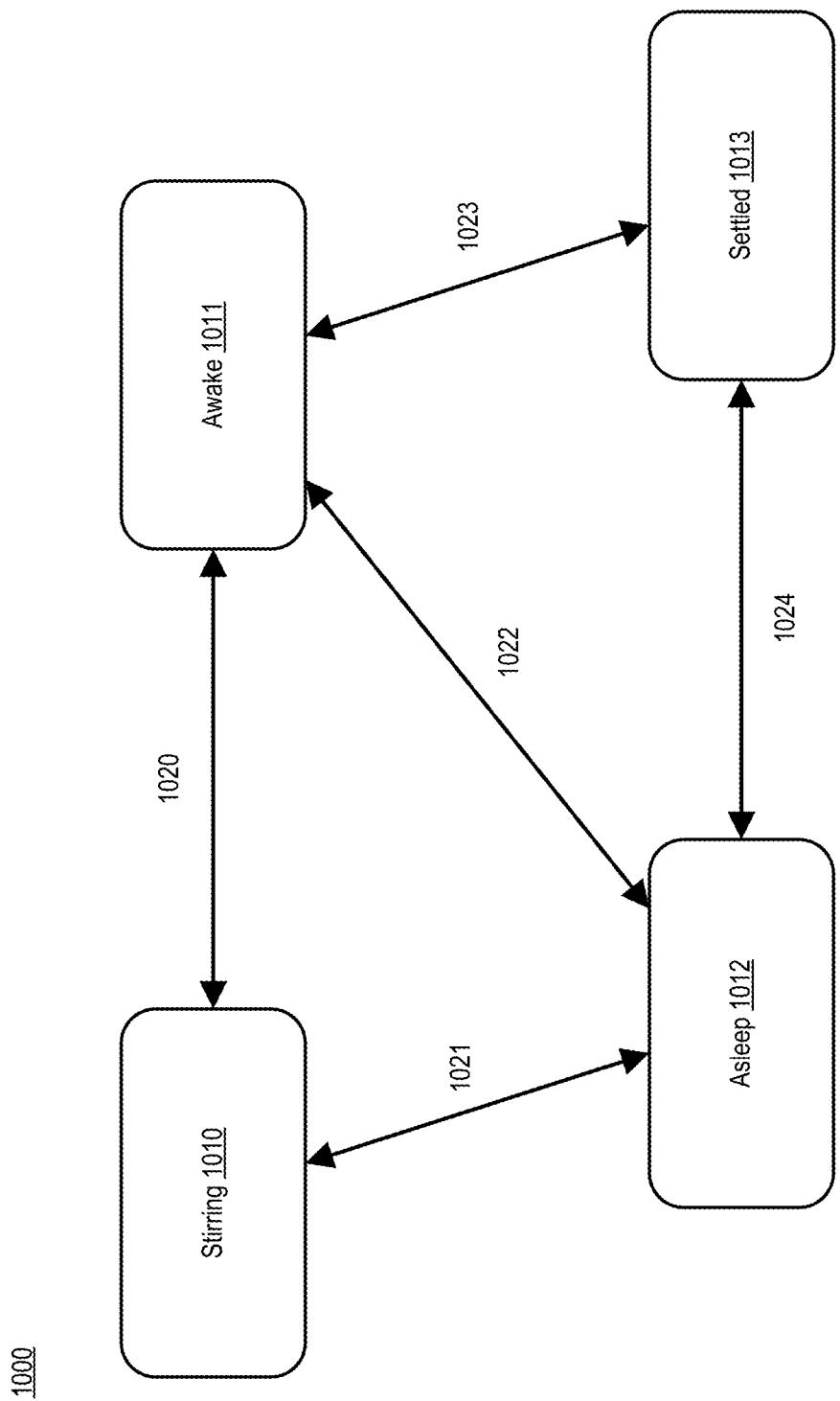
FIG. 10 is a state diagram of an exemplary state machine to determine activity levels, according to aspects of the present disclosure.

In some cases, activity monitor 110 can use a state machine to determine an activity state of an infant. An exemplary state machine is shown in FIG. 10. The state machine can be implemented by monitor 110, activity classification server 180, mobile device 199, or another device. The predicted state can be output to a caregiver on a periodic basis.

FIG. 10 is a state diagram of an exemplary state machine to determine activity levels, according to aspects of the present disclosure. FIG. 10 depicts state machine 1000, which includes various states and transitions between the states.

More specifically, state machine 1000 includes four states: stirring 1010, awake 1011, asleep 1012, and settled 1013. Other states are possible. State machine 1010 also includes examples of transitions between states. For example, transition 1020 is a transition between stirring 1010 and awake 1011. Transition 1021 is a transition between stirring 1010 and asleep 1012. Transition 1022 is a transition between awake 1011 and asleep 1012. Transition 1023 is a transition between awake 1011 and settled 1013. Finally, transition 1024 is a transition between asleep 1012 and settled 1013.

Transitions 1020-1024 can be trigged by detection of infant activity, e.g., by using methods 300 or 400.

In some cases, measurements from the accelerometer or gyroscope can cause short transitions in state. One example is when an infant is asleep but stirs during sleep for a short time, e.g., five minutes. Such a short periods can be erroneously labeled awake, causing a care giver to be concerned or frustrated with the monitor. In another example, an "asleep" state is preceded by a certain amount of settled time, which is really the infant going to sleep, e.g., calming down. Further, during the day, time periods of low activity can be erroneously measured as asleep.

In some cases, a user of the activity monitor may not expect or know how to act on such activity state detections. Accordingly, in some cases, activity monitor can use a smoothing filter to smooth out short or seemingly erratic transitions. An example of one such smoothing filter is depicted in FIG. 11 and is described further with respect to FIGS. 12-15.

Figure 11:
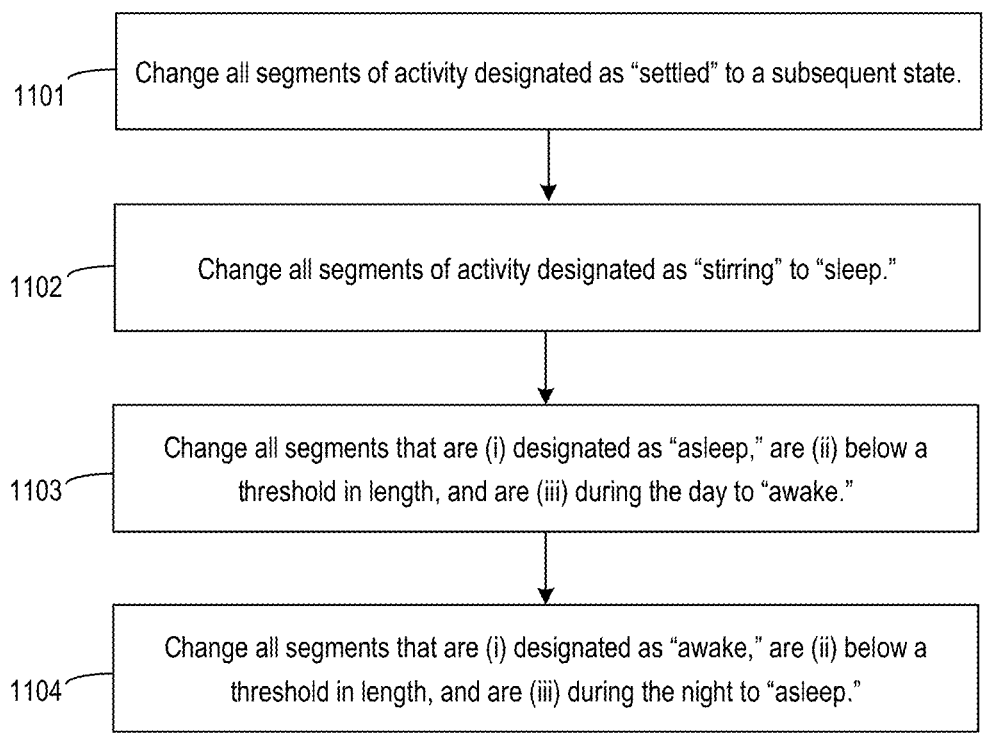
FIG. 11 is a flowchart of an exemplary method performed by a smoothing filter, according to certain aspects of the present disclosure.

FIG. 11 is a flowchart of an exemplary method 1100 performed by a smoothing filter, according to certain aspects of the present disclosure. For discussion purposes, FIG. 11 is explained with respect to FIGS. 12-15.

FIGS. 12-15 are diagrams illustrating exemplary operations performed by a smoothing filter, according to aspects of the present disclosure.

Figure 12:
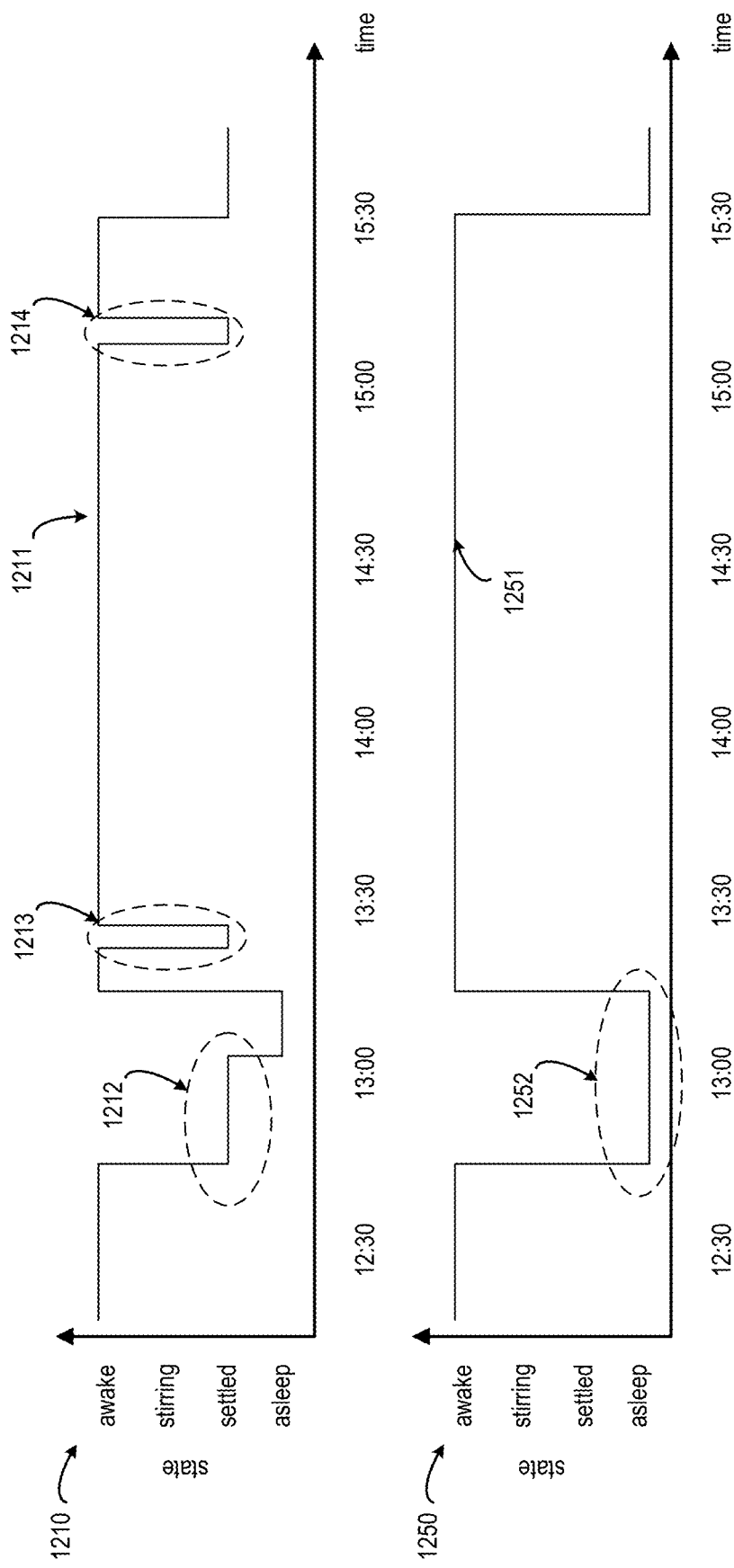
FIGS. 12-15 are diagrams illustrating exemplary operations performed by a smoothing filter, according to aspects of the present disclosure.

At block 1101, a smoothing filter changes all segments of activity designated as "settled" to a subsequent state. FIG. 12 depicts graphs 1210 and 1250, which each depict state ("awake," "stirring," "settled," and "asleep") over time. More specifically, graph 1210 depicts prediction 1211, which represents an output of the activity monitor at block 1101. Output 1251 represents the output after block 1101 has completed.

As can be seen, graph 1210 includes areas 1212, 1213, and 1214, which indicate transitions to the settled state. As depicted in area 1252, periods in which the predicted state transitioned from settled to asleep were re-classified as asleep. As depicted in output 1251 subsequent to area 1252, the transitions from settled to awake identified in areas 1213 and 1214 are converted to awake.

Figure 13:
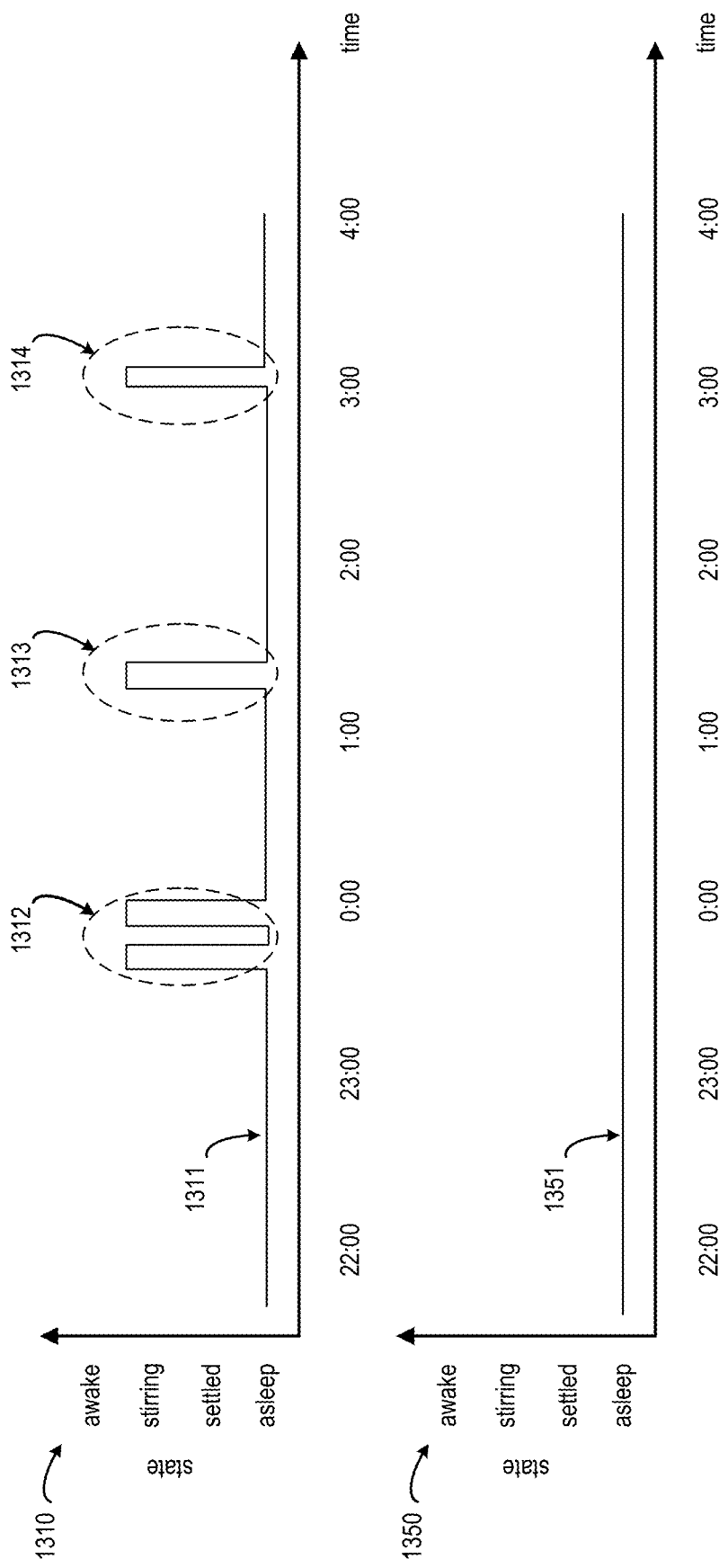

At block 1102, the smoothing filter changes all segments of activity designated as "stirring" to "sleep." FIG. 13 depicts graphs 1310 and 1350, which each depict a state over time. More specifically, graph 1310 depicts prediction 1311, which represents an input to the smoothing filter at block 1102. Graph 1351 represents the output after block 1101 has completed.

As can be seen, areas 1312, 1313, and 1314, each of which represents a brief time in which the state is "stirring" before and after periods of "asleep." Areas 1312-1314 are removed or "smoothed" by the smoothing filter. As can be seen, graph 1351 depicts a constant "asleep" state.

Figure 14:
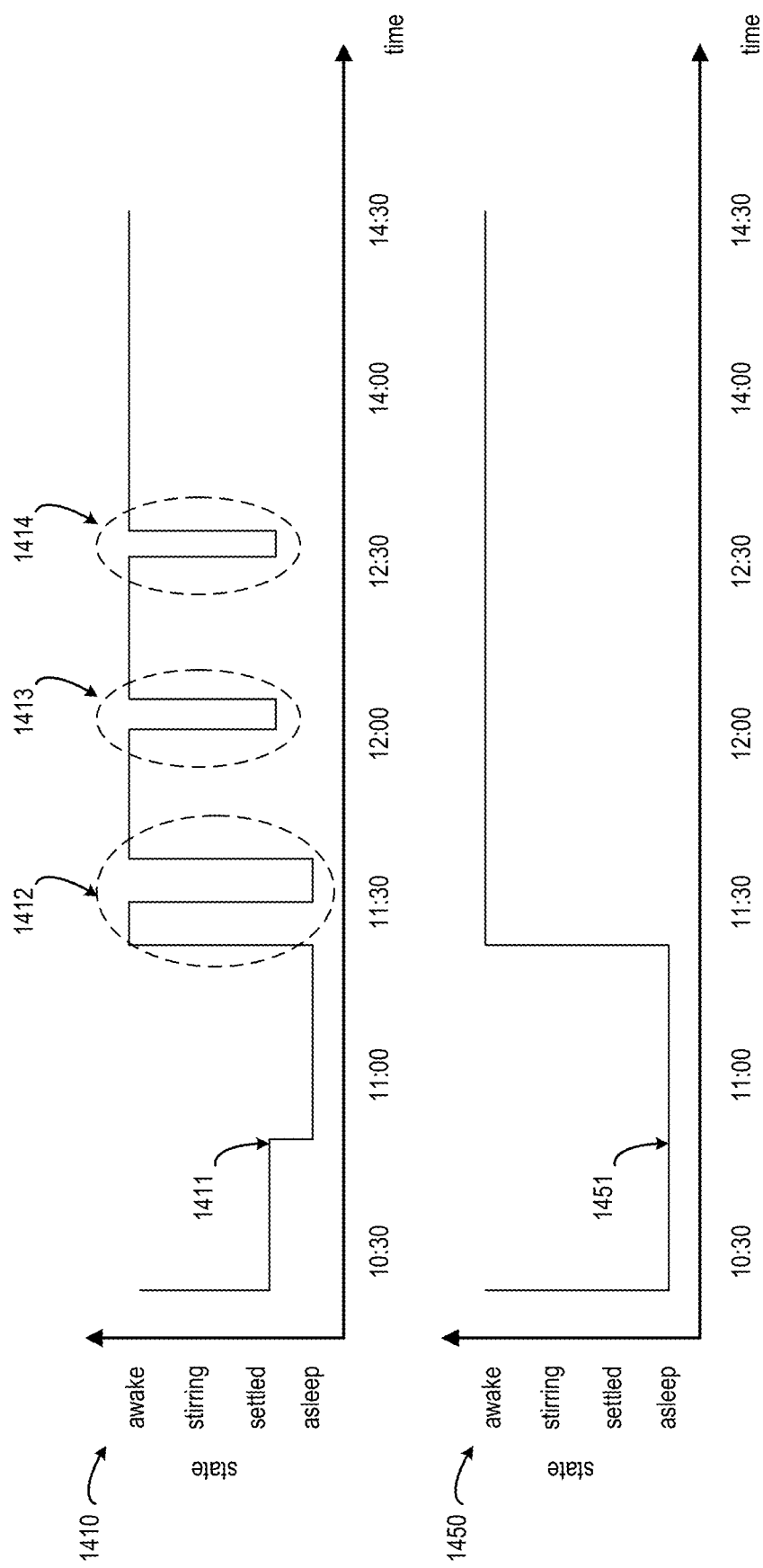

At block 1103, the smoothing filter changes all segments that are (i) designated as "asleep," are (ii) below a threshold in length, and are (iii) during the day to "awake." FIG. 14 depicts graphs 1410 and 1450, which each depict a state over time. More specifically, graph 1410 depicts prediction 1411, which represents an input to the smoothing filter at block 1103. Graph 1451 represents the output after block 1103 has completed.

As can be seen, areas 1412-1414 are areas in which the predicted state changes from awake to asleep to awake, remaining in the asleep state for only a short period of time. Such periods of activity may have been erroneously identified as asleep, because they are too short to really be asleep. Accordingly, the smoothing filter changes these states to awake, resulting in graph 1451. Examples of threshold in length (or time) include 10, 20, or 30 minutes.

Figure 15:
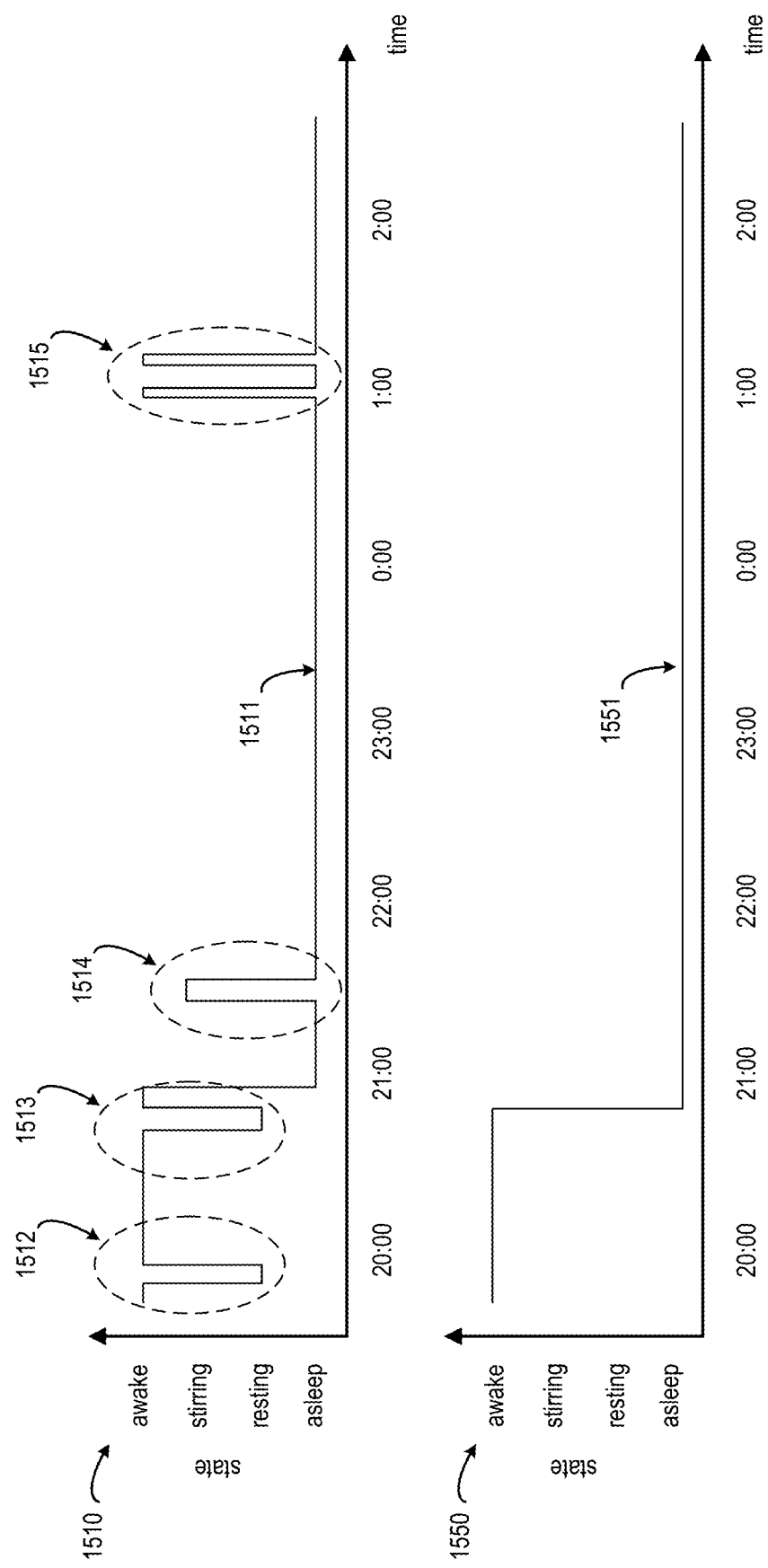

At block 1104, the smoothing filter changes all segments that are (i) designated as "awake," are (ii) below a threshold in length, and are (iii) during the night to "asleep." FIG. 15 depicts graphs 1510 and 1550, which each depict a state over time. More specifically, graph 1510 depicts prediction 1511, which represents an input to the smoothing filter at block 1104. Graph 1551 represents the output after block 1104 has completed. The output depicted in graph 1551 can be output to a user interface.

As can be seen, areas 1512-1515 represent areas predicted as "awake" within areas of "asleep." Such periods of activity may have been erroneously identified as awake, because they are too short to really be awake, given that the infant has been asleep for a relatively long period of time and continues to be asleep afterwards. Accordingly, the smoothing filter changes these states to asleep, resulting in graph 1551.

Alternatively, or in addition, monitor application 113 can display historical sleep information for the infant in graphical format or on a calendar display, to enable a caregiver to visual sleep trends or routines.

Figure 16:
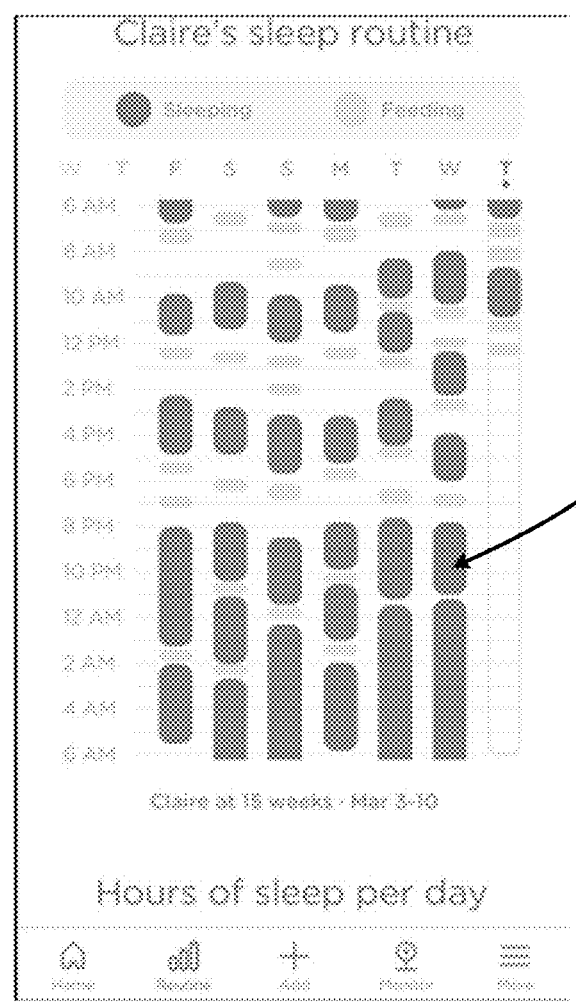
FIGS. 16 and 17 depict exemplary user interfaces for viewing sleep patterns of an infant, according to certain aspects of the present disclosure.
Figure 17:

FIGS. 16 and 17 depict exemplary user interfaces for viewing sleep patterns of an infant, according to certain aspects of the present disclosure. FIG. 16 includes user interface 1600 and graph 1601. User interface 1600 includes a sleep routine display that indicates, for multiple days of the week and for each time period during the day, whether an infant subject was predicted to be asleep or awake. FIG. 17, which includes user interface 1700, shows the total sleep per day for an infant in graph 1701. Graph 1701 can be filtered based on a weekly, monthly, or lifetime basis.

Monitor application 113 can also output feeding information derived from the activity of the infant. For example, output device 111 can provide information about when the last feeding occurred, how long a feeding event last, and whether a nursing event took place on the left or the right breast. Monitor application 113 may also enable caregivers to input information from bottle feeding events. Monitor application 113 can display historical feeding information for the infant in graphical format or on a calendar display, to enable a caregiver to visualize feeding trends or routines.

Figure 18:
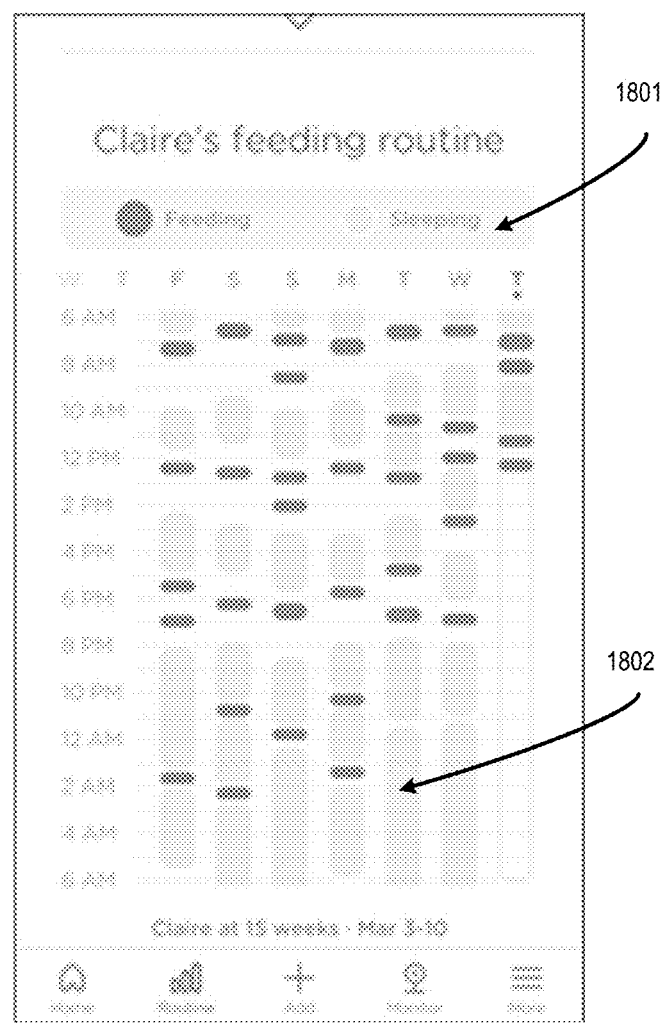
FIGS. 18-20 depict exemplary user interfaces for viewing feeding patterns of an infant, according to certain aspects of the present disclosure.

FIG. 18 depicts exemplary user interfaces for viewing feeding patterns of an infant, according to certain aspects of the present disclosure. FIG. 18 includes user interface 1800, sleeping or feeding key 1801, and graph 1802. Graph 1802, which is read in conjunction with feeding key 1801, shows time periods of each day for multiple days, whether an infant subject was sleeping, feeding, or neither.

Figure 19:
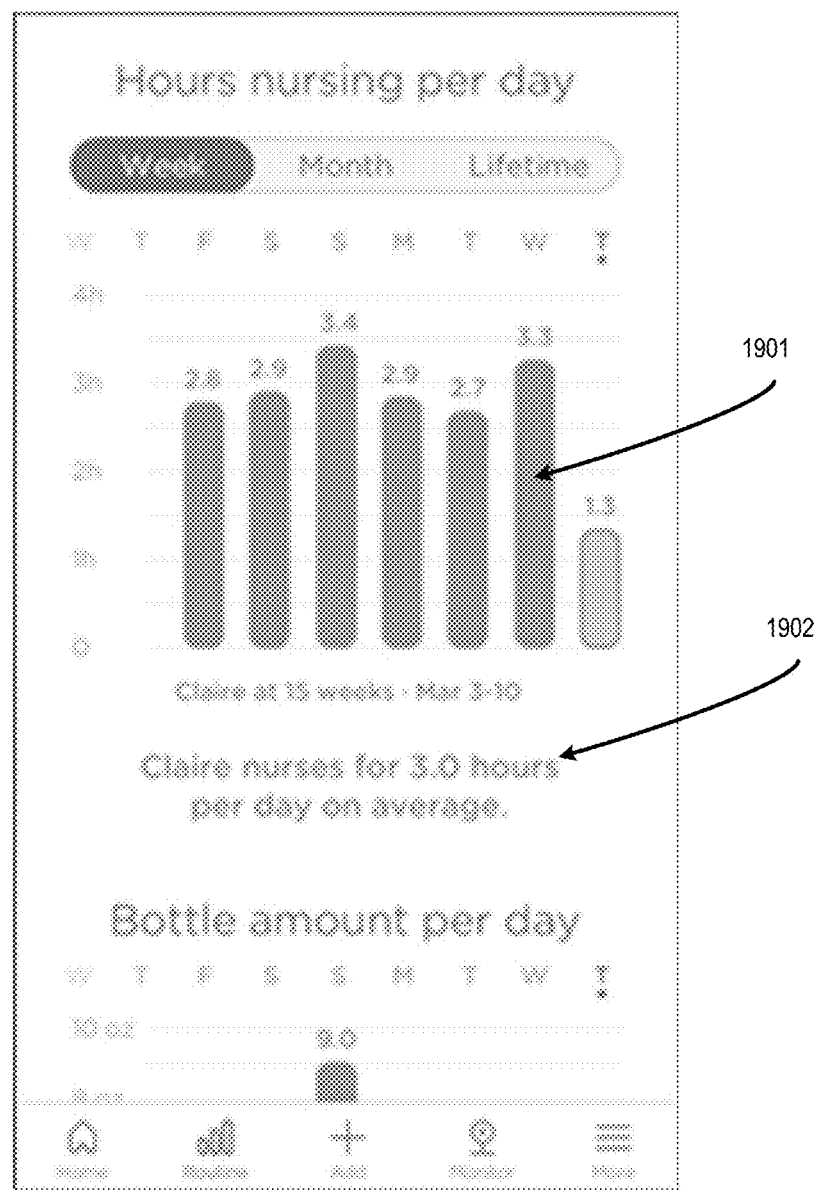

FIG. 19 includes user interface 1900, which depicts graph 1901, and textual information 1902. User interface 1900 allows filtering by week, month, or lifetime. Graph 1901 shows the hours spent feeding, or nursing, each day. Textual information 1902 provides specific feedback to an operator such as averages.

Figure 20:
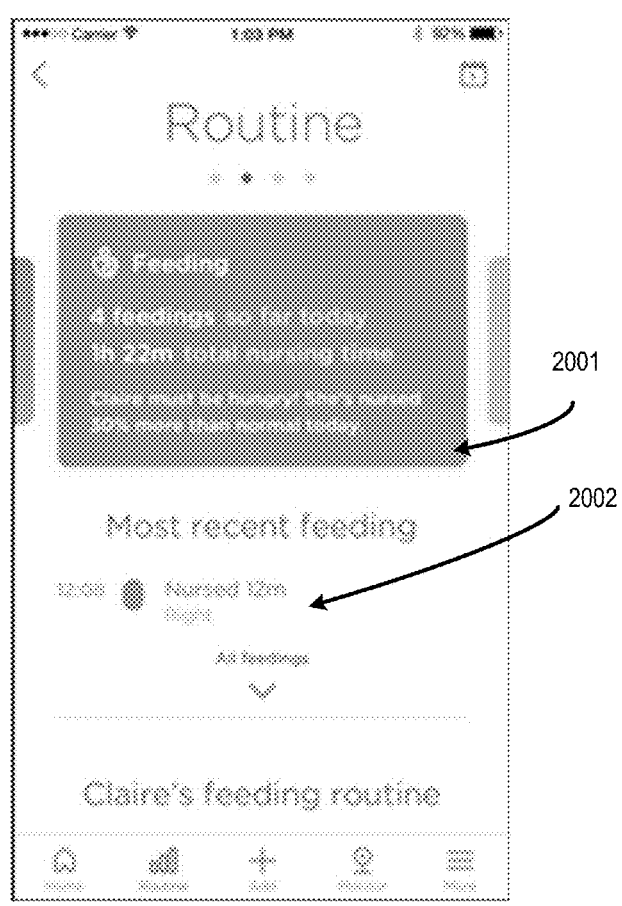

FIG. 20 includes user interface 2000, which depicts textual information box 2001 and recent information 2002. Textual information box 2001 provides an operator of the device detailed information such as number of feedings for the current day, total time nursed for the day, and observations. Recent information 2002 shows the last feeding time and duration.

Figure 21:
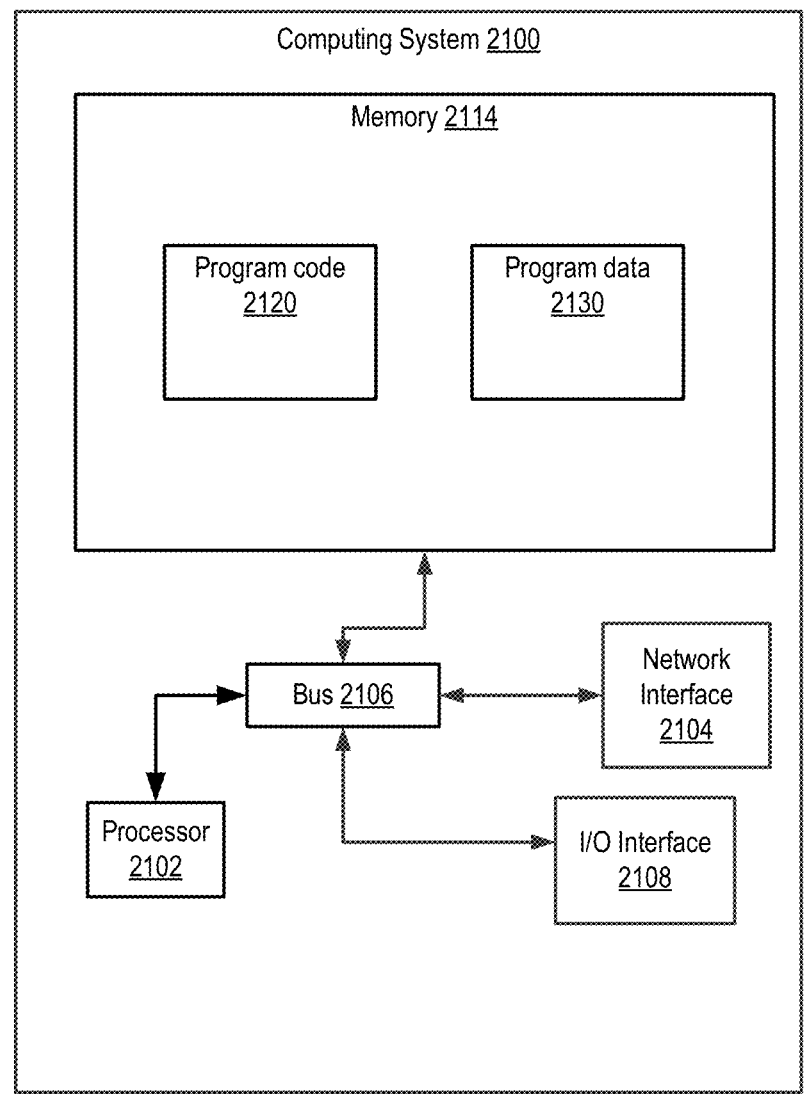
FIG. 21 depicts a block diagram of a processor configured to determine activity of a wearer of a sensor, according to certain aspects of the present disclosure.

FIG. 21 depicts a block diagram of a processor configured to determine activity of a wearer of a sensor, according to certain aspects of the present disclosure. Some or all of the components of the computing system 2100 can belong to the processor 105 or processor 112 of FIG. 1. For example, monitor application 113 and predictive model 120 may operate on the computing system 2100. The computing system 2100 includes one or more processors 2102 communicatively coupled to one or more memory devices 2114. The processor 2102 executes computer-executable program code, which can be in the form of non-transitory computer-executable instructions, stored in the memory device 2114, accesses information stored in the memory device 2114, or both. Examples of the processor 2102 include a microprocessor, an application-specific integrated circuit ("ASIC"), a field-programmable gate array ("FPGA"), or any other suitable processing device. The processor 2102 can include any number of processing devices, including one.

The memory device 2114 includes program code 2120 and program data 2130. Program code 2120 can include code executed by monitor application 113, predictive model 120, predictive model 190, a mobile application executing on mobile device 199, or any other application described herein. Program data 2130 can include training data for predictive models, acceleration or gyroscope measurements, or program data for any application described herein such as monitor application 113, predictive model 120, or predictive model 190.

The memory device 2114 includes any suitable computer-readable medium such as electronic, optical, magnetic, or other storage device capable of providing a processor with computer-readable instructions or other program code. Non-limiting examples of a computer-readable medium include a magnetic disk, a memory chip, a ROM, a RAM, an ASIC, optical storage, magnetic tape or other magnetic storage, or any other medium from which a processing device can read instructions. The instructions may include processor-specific instructions generated by a compiler or an interpreter from code written in any suitable computer-programming language, including, for example, C, C++, C#, Visual Basic, Java, Python, Perl, JavaScript, and ActionScript.

The computing system 2100 may also include a number of external or internal devices such as input or output devices. For example, the computing system 2100 is shown with an input/output ("I/O") interface 2108 that can receive input from input devices or provide output to output devices. A bus 2106 can also be included in the computing system 2100. The bus 2106 can communicatively couple one or more components of the computing system 2100 and allow for communication between such components.

The computing system 2100 executes program code that configures the processor 2102 to perform one or more of the operations described above with respect to FIG. 1-4 or 9-11. The program code of the monitor application 113, which can be in the form of non-transitory computer-executable instructions, can be resident in the memory device 2114 or any suitable computer-readable medium and can be executed by the processor 2102 or any other one or more suitable processor. Execution of such program code configures or causes the processor(s) to perform the operations described herein with respect to the processor 2102. In additional or alternative aspects, the program code described above can be stored in one or more memory devices accessible by the computing system 2100 from a remote storage device via a data network. The processor 2102 and any processes can use the memory device 2114. The memory device 2114 can store, for example, additional programs, or data used by the applications executing on the processor 2102 such as the monitor application 113.

The computing system 2100 can also include at least one network interface 2104. The network interface 2104 includes any device or group of devices suitable for establishing a wired or wireless data connection to one or more data networks. Non-limiting examples of the network interface 2104 include an Ethernet network adapter, WiFi network, a modem, and/or the like. The computing system 2100 is able to communicate with one or more other computing devices or computer-readable data sources via a data network using the network interface 2104.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multi-purpose microprocessor-based computer systems accessing stored software that programs or configures the computing system from a general purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

That which is claimed is:

1. A computer-implemented method for determining activity of an infant, the method comprising:
    receiving, from an inertial measurement sensor on an infant monitoring device, a plurality of inertial measurements in three dimensions for a time period;
    calculating, using a processor of the infant monitoring device, statistical data derived from the inertial measurements;
    providing, via the processor, the plurality of inertial measurements and the statistical data to a predictive model;
    receiving, via the processor, from the predictive model of the infant monitoring device and for the time period, a determined activity from a plurality of predefined activities based on the inertial measurements, wherein the plurality of predefined activities comprises awake, asleep, stirring, and settled;
    responsive to identifying, via the processor, that the determined activity is settled and a previously determined activity is awake, asleep, or stirring, adjusting the determined activity to be one of awake, asleep, or stirring;
    responsive to identifying, via the processor, that the determined activity is stirring and the previously determined activity is asleep, changing the determined activity to asleep; and
    providing the determined activity to an output device.

2. The method of claim 1, wherein the statistical data comprises (i) a variance of the plurality of inertial measurements, or (ii) a root-mean-square of the plurality of the inertial measurements.

3. The method of claim 1, wherein the plurality of predefined activities comprises one or more of (i) asleep, (ii) awake, (iii) lying on abdomen, (iv) lying on back, (v) settled, or (vi) stirring.

4. The method of claim 1, wherein stirring represents movement more than a first threshold amount and wherein settled represents movement less than a second threshold amount.

5. The method of claim 1, further comprising:
    responsive to identifying, via the processor, that the determined activity is (i) asleep, is (ii) below a threshold amount, and (iii) occurred during daytime, changing the determined activity to awake; and
    responsive to identifying, via the processor, that the determined activity is (i) awake, is (ii) below a threshold amount, and (iii) occurred during nighttime, changing the determined activity to asleep.

6. The method of claim 1, wherein the plurality of predefined activities comprise (i) whether an infant is nursing, (ii) whether the infant was bottle feeding, or (iii) an orientation of the infant during feeding, the method further comprising:
    receiving, from a gyroscope, a plurality of orientation or angular velocity measurements; and
    providing, via the processor, the plurality of orientation or angular velocity measurements to the predictive model, wherein the determined activity is based at least in part on the angular velocity measurements.

7. The method of claim 1, further comprising:
    receiving via the processor, training data comprising time series data indicating inertial measurements measured over a plurality of time periods, the training data annotated with a plurality of training labels indicating, for each time period, a corresponding activity of a plurality of activities; and
    iteratively adjusting, via the processor, the predictive model based on a loss function that is based on a comparison of a prediction to a respective training label, wherein iteratively adjusting the predictive model comprises:
        determining, by the predictive model, a prediction of whether data corresponding to a time period corresponds to one of the plurality of activities, and
        modifying, via the processor, the predictive model such that a subsequent value of the loss function is decreased in a subsequent iteration.

8. The method of claim 1, further comprising:
    receiving, via the processor and from a monitor device, additional training data comprising time series data indicating inertial measurements measured over an additional time period, the additional training data annotated with a training label indicating a corresponding activity of a plurality of activities; and
    updating, via the processor, the predictive model based on the additional training data and a loss function, the updating comprising:
        determining, by the predictive model, a prediction of whether data corresponding to a time period corresponds to one of the plurality of activities, and
        reducing a value of the loss function based on a comparison of the prediction to the training label.

9. The method of claim 1, further comprising:
    receiving, via the processor, training data comprising time series data indicating inertial measurements measured over a plurality of time periods, the training data annotated with a plurality of training labels indicating, for each time period, whether an infant was awake or asleep; and
    training, via the processor, the predictive model based on the training data and a loss function, the training comprising:
        determining, by the predictive model, a prediction of (i) awake, (ii) asleep, (iii) stirring, or (iv) settled, and
        minimizing the loss function based of a comparison of the prediction to the training label.

10. The method of claim 1, further comprising:
storing, in a memory of the infant monitoring device, time series data for a plurality of time periods;
determining, via the processor and based on the predictive model, a plurality of activities, each corresponding to a different one of the plurality of time periods; and
responsive to determining, via the processor, that a predetermined time threshold has elapsed, generating a log report comprising, for each of the plurality of time periods, the determined activity and displaying the log report on a user interface.

11. The method of claim 1, further comprising:
receiving, over a wireless transceiver, a software update comprising a new predictive model; and
updating, via the processor, the predictive model with the new predictive model.

12. An infant monitoring device configured to determine an activity of an infant, the infant monitoring device comprising:
an inertial measurement sensor; and
a processor configured to perform operations comprising:
receiving, from the inertial measurement sensor, a plurality of inertial measurements in three dimensions for a time period;
calculating statistical data derived from the inertial measurements;
providing the plurality of inertial measurements and the statistical data to a predictive model;
receiving, from the predictive model and for the time period, and based on the inertial measurements, a breathing rate for an infant;
receiving, from the predictive model, a determined activity of the infant from a plurality of predefined activities based on the inertial measurements, wherein the plurality of predefined activities comprises awake, asleep, stirring, and settled and wherein stirring represents movement more than a first threshold amount and wherein settled represents movement less than a second threshold amount; and
providing the determined activity and the breathing rate to an output device.

13. The infant monitoring device of claim 12, the operations further comprising receiving, from the predictive model, a volume of liquid consumed by the infant during feeding.

14. The infant monitoring device of claim 12, the operations further comprising receiving, from the predictive model, an estimation of (i) a time until a next feeding or (ii) a volume of liquid expected to be consumed at the next feeding.

15. The infant monitoring device of claim 12, wherein the inertial measurement sensor can be attached to or removed from an absorbent article.

16. The infant monitoring device of claim 12, wherein the inertial measurement sensor is configured to be attached to an absorbent article and not to a body of an infant.

17. An infant monitoring system comprising:
a monitoring device comprising:
a first wireless transceiver; and
a first processor configurable to execute instructions that cause the first processor to:
receive an acceleration measurement from the first wireless transceiver of a sensing device;
provide the acceleration measurement to a predictive model;
receive, from the predictive model and based on the acceleration measurement, a determined activity from a plurality of predefined activities;
responsive to identifying that the determined activity is settled and a previously determined activity is awake, asleep, or stirring, adjust the determined activity to be one of awake, asleep, or stirring;
responsive to identifying that the determined activity is stirring and the previously determined activity is asleep, change the determined activity to asleep; and
provide the determined activity to an output device, wherein the sensing device comprises:
an accelerometer configured to sense acceleration in at least one degree of freedom,
a second wireless transceiver; and
a second processor configured to execute instructions that cause the second processor to:
receive, from the accelerometer, the acceleration measurement; and
provide the acceleration measurement to the first wireless transceiver.

18. The infant monitoring system of claim 17, wherein the output device is external to the monitoring device and wherein providing the determined activity to an output device comprises transmitting the determined activity over a data network connection to the output device.

19. The infant monitoring system of claim 17, wherein providing the acceleration measurement to a predictive model comprises transmitting the acceleration measurement over a network to a server device, and wherein receiving the determined activity further comprises receiving the determined activity over the network from the server device.

20. The infant monitoring system of claim 17, wherein the first processor is further configurable to execute instructions that cause the first processor to:
store, in a memory, time series data for a plurality of time periods;
determine, based on the predictive model, a plurality of activities, each corresponding to a different one of the plurality of time periods; and
responsive to determining that a predetermined time threshold has elapsed, generate a log report comprising the plurality of activities and corresponding time periods.

21. The infant monitoring system of claim 17, wherein the first processor is further configurable to execute instructions that cause the first processor to:
transmit, over a data network, the acceleration measurement to a server device configured to log a plurality of measurements from a plurality of infant monitoring systems.

22. The infant monitoring system of claim 17, wherein the plurality of predefined activities comprises (i) awake, (ii) asleep, (iii) stirring, or (iv) settled, and the first processor is further configurable to execute instructions that cause the first processor to:
responsive to identifying that the determined activity is (i) asleep, is (ii) below a first threshold amount, and (iii) occurred during daytime, changing the determined activity to awake; and
responsive to identifying that the determined activity is (i) awake, is (ii) below a second threshold amount, and (iii) occurred during nighttime, changing the determined activity to asleep.

23. The infant monitoring system of claim 17, further comprising an additional sensor, wherein:
- the first processor is configurable to execute instructions that cause the first processor to:
  - receive, from the additional sensor, an additional measurement of (i) a change in electrical conductivity, (ii) a change in optical properties, (iii) a change in capacitance, (iv) a change in color, or (v) a change in detected volatile organic compound; and
  - transmit the additional measurement via the first wireless transceiver to the monitoring device,
- wherein the sensing device is configurable to execute instructions that cause the second processor to:
  - receive, via the second wireless transceiver, the additional measurement from the first wireless transceiver;
  - determine, from the additional measurement, an indication of a presence of (i) urine, or (ii) bowel movement; and
  - provide the indication to the output device.

24. A wearable device configured to determine wetness in an absorbent article worn by an infant and to determine an activity of the infant, the wearable device comprising:
- a processor;
- an optical sensor configured to:
  - obtain a color measurement relating to the absorbent article; and
  - transmit the color measurement to the processor; and
- an inertial measurement sensor configured to:
  - detect a plurality of inertial measurements caused by the infant; and
  - provide the plurality of inertial measurements to the processor, wherein the processor is configured to:
    - receive, from the inertial measurement sensor, the plurality of inertial measurements;
    - provide the plurality of inertial measurements to a predictive model;
    - receive, from the predictive model, a determined activity of the infant from a plurality of predefined activities based on the inertial measurements, wherein the plurality of predefined activities comprises awake, asleep, stirring, and settled, and wherein stirring represents movement more than a first threshold amount and wherein settled represents movement less than a second threshold amount;
    - determine, from the color measurement, an indication of wetness in an absorbent article; and
    - provide the determined activity and the indication of wetness to an output device.

25. The wearable device of claim 24, further comprising a battery operable to power the processor and the inertial measurement sensor.

* * * * *